US007183050B2

(12) United States Patent
Krull

(10) Patent No.: US 7,183,050 B2
(45) Date of Patent: Feb. 27, 2007

(54) GRADIENT RESOLVED INFORMATION PLATFORM

(76) Inventor: Ulrich J. Krull, 1920 Sandown Road, Mississauga, Ontario L5M 2Z8 (CA)

(*) Notice: Subject to any disclaimer, the term of this patent is extended or adjusted under 35 U.S.C. 154(b) by 0 days.

(21) Appl. No.: 10/126,504

(22) Filed: Apr. 18, 2002

(65) Prior Publication Data
US 2003/0055233 A1 Mar. 20, 2003

Related U.S. Application Data

(60) Provisional application No. 60/284,715, filed on Apr. 18, 2001.

(51) Int. Cl.
C12Q 1/68 (2006.01)
C12M 1/36 (2006.01)
C07H 21/04 (2006.01)

(52) U.S. Cl. .................. 435/6; 435/174; 435/283.1; 435/287.2; 536/23.1; 536/24.3

(58) Field of Classification Search .............. 435/6, 435/174, 283.1, 287.2, 287.9; 536/23.1, 536/24.3
See application file for complete search history.

(56) References Cited

U.S. PATENT DOCUMENTS

| 5,175,209 A | 12/1992 | Beattie et al. ............ 525/54.11 |
| 5,436,327 A | 7/1995 | Southern et al. .......... 536/25.34 |
| 5,599,668 A * | 2/1997 | Stimpson et al. ............... 435/6 |
| 5,866,330 A * | 2/1999 | Kinzler et al. ................. 435/6 |
| 6,045,671 A | 4/2000 | Wu et al. ............... 240/298.11 |
| 6,218,116 B1 | 4/2001 | Ginot ............................. 435/6 |
| 6,271,044 B1 * | 8/2001 | Ballerstadt et al. ......... 436/518 |
| 6,379,897 B1 * | 4/2002 | Weidenhammer et al. ..... 435/6 |
| 6,471,916 B1 * | 10/2002 | Noblett .................... 422/82.08 |

(Continued)

FOREIGN PATENT DOCUMENTS

WO     WO 95/26416     10/1995

(Continued)

OTHER PUBLICATIONS

Abel, A.P. et al. (1996), "Fiber-Optic Evanescent Wave Biosensor for the Detection of Oligonucleotides," Anal. Chem. 68:2905-2912.

(Continued)

Primary Examiner—B J Forman
(74) Attorney, Agent, or Firm—Christensen O'Connor Johnson Kindness PLLC

(57) ABSTRACT

Methods and devices for the detection and identification in a sample of one or more target molecules which bind to nucleic acid probe molecules are provided. The method includes contacting the sample with a surface that is coated with one or more gradients of nucleic acid or nucleic acid analog probe molecules that bind target molecules in the sample. Gradients are formed by varying a physical, structural or functional property of the probes on the surface; for example, the density of probe molecules bound to the surface. The coating layer or immobilization layer in which the gradient is formed is preferably continuous Determination of the location, speed and/or extent of hybridisation of a nucleic acid on a gradient surface is useful to identify target molecules bound to probes and/or to quantitatively measure the amount of the target in a sample.

30 Claims, 4 Drawing Sheets

U.S. PATENT DOCUMENTS

| | | | |
|---|---|---|---|
| 6,503,711 B1 | 1/2003 | Krull et al. | 435/6 |
| 2002/0137074 A1 | 9/2002 | Piunno et al. | 435/6 |
| 2003/0157538 A1 | 8/2003 | Krull et al. | 435/6 |

FOREIGN PATENT DOCUMENTS

| | | | |
|---|---|---|---|
| WO | WO 97/33169 | | 9/1997 |
| WO | WO 98/00402 | | 1/1998 |
| WO | WO 98/47613 | | 10/1998 |
| WO | WO 98/58079 | | 12/1998 |
| WO | WO 99/35289 | * | 7/1999 |
| WO | WO 00/04390 | | 1/2000 |

OTHER PUBLICATIONS

Agrawal et al. (1990), "Site specific functionalization of oligonucleotides for attaching two different reporter groups," Nucl. Acids Res. 18:5419-5423.

Beaucage et al. (1992), "Advances in the Synthesis of Oligonucleotides by the Phosphoramidite Approach," Tetrahedron 48(12):2223-2311.

Beaucage and Iyer (1993), "The Functionalization of Oligonucleotides Via Phosphoramidite Derivatives," Tetrahedron 49:10:1925-1963.

Bianchi, N. et al. (1997), "Biosensor technology and surface plasmon resonance for real-time detection of HIV-1 genomic sequences amplified by polymerase chain reaction," Clinical and Diagnostic Virology 8:199-208.

Bier, F.F. and Scheller, F.W. (1996), "Label-free observation of DNA-hybridisation and endonuclease activity on a wave guide surface using a grating coupler," Biosensors and Bioelectron. 11:669-674.

Blonder, R. et al. (1996), "Application of Redox Enzymes for Probing the Antigen-Antibody Association at Monolayer Interfaces: Development of Amperometric Immunosensor Electrodes" Anal. Chem. 68:3151-3157.

Brennan et al. (1990), "Fluorescence transduction of an enzyme-substrate reaction by modulation of lipid membrane structure," Anal. Chim. Acta 237:253-263.

Brennan et al. (1993), "Covalent immobilization of amphiphilic monolayers containing urease onto optical fibers for fluorimetric detection of urea," Sensors and Actuators B 11:109-119.

Burger, D.R. (1993), "Novel Antisense Technology: Therapeutic and Diagnostic Applications," J. Clin. Immun. L6:224-230.

Chee, M. et al. (1996), "Accessing Genetic Information with High-Density DNA Arrays," Science 274:610-614.

Englisch et al. (1991), "Chemically Modified Oligonucleotides as Probes and Inhibitors," Angew Chem. Int. Ed. Eng. 30(6):613-629.

Foder, S.P.A. et al. (Feb. 1991), "Light-Directed, Spatially Addressable Parallel Chemical Synthesis," Science 251:767-773.

Ghosh and Musso (1987), "Covalent attachment of oligonucleotides to solid supports," Nucl. Acids Res. 15:5353-5373.

Glass, T.R. et al. (1987), "Effect of numerical aperture on signal level in cylindrical waveguide evanescent fluorosensors," Appl. Opt. 26:2181-2187.

Goodchild (1990), "Conjugates of Oligonucleotides and Modified Oligonucleotides: A Review of Their Synthesis and Properties," J. Bioconjugate Chem. 1:165-187.

Gotoh, M. et al. (1994), "A novel approach for determination of mismatch formation effects on DNA hybridization kinetics using a biosensro," Nucl. Acids Symp. Series No. 31:121-122.

Graham, C.R. et al. (1992), "Gene probe assays on a fibre-optic evanescent wave biosensor," Biosensors and Bioelectron. 7:487-493.

Jenkins et al. (1992), "A Sequence-Specific Molecular Light Switch: Tethering of an Oligonucleotide to a Dipyridophenazine Complex of Ruthenium (II)," J. Am. Chem. Soc. 114:8736-8738.

Kern, W. and Puotinen, D.A. (1970), "Cleaning Solutions Based on Hydrogen Peroxide for use in Silicon Semiconductor Technology," RCA Rev. 6:187-206.

Kleinjung, F. et al. (1997), "Fibre-optic genosensor for specific determination of femtomolar DNA oligomers," Anal. Chim. Acta 350:51-58.

Krull et al. (1997), "A Fiber Optic DNA Sensor for Rapid Detection of Environmental E. coli," Proc. ofNATO ARW on Biosensors for Direct Monitoring of Environmental Pollutants in Field, Kluwer Acad. Pub., ASI Series 2, 38:67-77.

Lee, L.G. et al. (1986), "Thiazole Orange: A New Dye for Reticulocyte Analysis," Cytometry 7:508-517.

Lesnik et al. (1993), "Oligodeoxynucleotides Containing 2'-O-Modified Adenosine: Synthesis and Effects on Stability of DNA:RNA Duplexes," Biochemistry 32:7832-7838.

Love, W.F. et al. (1991), "Optical Characteristics of Fiberoptic Evansecent Wave Sensors," in *Biosensors with Fibre Optics*, Wise and Wingard (eds.), The Humana Press, Inc., pp. 139-180.

Maskos, U. and Southern, E.M. (1992), "Oligonucleotide hybridisations on glass supports: a novel linker for oligonucleotide synthesis and hybridisation properties of oligonucleotides synthesised in situ," Nucl. Acids Res. 20(7):1679-1684.

Maskos, U. and Southern, E. (1993), "A study of oligonucleotide reassocation using large arrays of oligonucleotides synthesised on a glass support," Nucl. Acids Res. 21(20):4663-4669.

McGall, G. et al. (1996), "Light-directed synthesis of high-density oligonucleotide arrays using semiconductor photoresists," Proc. Natl. Acad. Sci. 93:13555-13560.

McGall, G.H. et al. (1997), "The Efficiency of Light-Directed Synthesis of DNA Arrays on Glass Substrates," J. Am. Chem. Soc. 119:5081-5090.

Meier, C. and Engels, J.W. (1992), "Peptide Nucleic Acids (PNAs)—Unusual Properties of Nonionic Oligonucleotide Analogues," Angew. Chem. Int. Ed. Engl. 31(8):1008-1010.

Michael, K.L. et al. (1998), "Randomly Ordered Addressable High-Density Optical Sensor Arrays," Anal. Chem. 70:1242-1248.

Nielsen et al. (1993), "Peptide nucleic acids (PNAs): Potential anti-sense and anti-gene agents," Anti-Cancer Drug Design 8:53-63.

Nilsson, P. et al. (1995), "Real-Time Monitoring of DNA Manipulations Using Biosensor Technology," Anal. Biochem. 224:400-408.

O'Donnell-Maloney, M.J. and Little, D.P. (1996), "Microfabrication and array technologies for DNA sequencing and diagnostics," Genetic Analysis: Biomolecular Engineering 13:151-157.

Pieles et al. (1990), "A protected biotin containing deoxycytidine building block for solid phase synthesis of biotinylated oligonucleotides," Nucl. Acids Res. 18:4355-4360.

Piunno, P.A.E. (Nominally released Oct. 2001), "Development of a Fibre Optic Biosensor for Determination of Interfacial Nucleic Acid Hybrid Formation," Doctoral Thesis, University of Toronto.

Pon, R.T. (1993), "Solid-Phase Supports for Oligonucleotide Synthesis," in *Methods in Molecular Biology: Protocols for Oligonucleotides and Analogs*, vol. 20, S. Agrawal (ed.), Humana Press, Inc., Totowa, p. 465-496.

Roduit et al. (1987), "Synthesis of Oligodeoxyribonucleotides Containing an Aliphatic Amino Linker Arm at Selected Adenine Bases and Derivatization With Biotin," Nucleosides and Nucleotides 6:349-352.

Schutz, R. et al. (Apr. 2000), "Olefinic Peptide Nucleic Acids (OPAs): New Aspects of the Molecular Recognition of DNA by PNA," Angew. Chem. Int. Ed. 39(7):1250-1253.

Sheldon, E.L. et al. (1993), "Matrix DNA Hybridization," Clin. Chem. 39:718-719.

Sojka, B. et al. (1999), "Evaluating the quality of oligonucleotides that are immobilized on glass supports for biosensor development," Anal. Chim. Acta. 395:273-284.

Sojka et al. (Oct. 2000), "A Novel Phosphoramidite Method for Automated Synthesis of Oligonucleotides on Glass Supports for Biosensor Development," Appl. Biochem. Biotechnol. 89:85-103.

Sosnowski, R.G. et al. (1997), "Rapid determination of single base mismatch mutations in DNA hybrids by direct electric field control," Proc. Natl. Acad. Sci. USA 94:1119-1123.

Sowa et al. (1975), "The Facile Synthesis of R'-Nucleotides by the Selective Phosphorylation of a Primary Hydroxyl Group of Nucleosides with Phosphoryl Chloride," Bull. Chem. Soc. Jpn. 48:2084-2090.

Thompson, M. and Krull, U.J. (1984), "Biosensors and bioprobes," Trends in Analytical Chemistry 3:173-178.

Thompson, M. and Krull, U.J. (1991), "Biosensors and the Transduction of Molecular Recognition," Anal. Chem. 63:393A-405A.

Thompson, M. and Furtado, L.M. (Aug. 1999), "High density oligonucleotide and DNA probe arrays for the analysis of target DNA," Analyst 124:1133-1136.

Uddin, A.H. et al. (1997), "A fiber optic biosensor for fluorimetric detection of triple-helical DNA," Nucl. Acids Res. 25:4139-4146.

Uhlmann et al. (1993), "Oligonucleotide Analogs Containing ephospho-Internucleoside Linkages," in *Methods in Molecular Biology* 20: Protocols for Oligonucleotides and Analogs, S. Agrawal (ed.), Humana Press, NJ, pp. 355-389.

Uhlmann and Peymen, A. (1990), "Antisense Oligonucleotides: A New Therapeutic Principle," Chem. Rev. 90:543-584.

Watterson et al. (Apr. 2000), "Effects of Oligonucleotide Immobilization Density on Selectivity of Quantitative Transduction of Hybridization of Immobilized DNA," Langmuir 16:4984-4992.

Watterson, J.H. et al. (Apr. 2001), "Controlling the density of nucleic acid oligomers on fiber optic sensor for enhancement of selectivity and sensitivity," Sensors and Actuators B 74:27-36.

* cited by examiner

GRADIENT RESOLVED INFORMATION PLATFORM

CROSS-REFERENCE TO RELATED APPLICATIONS

This application takes priority under 35 USC 119(e) from U.S. provisional application Ser. No. 60/284,715, filed Apr. 18, 2001 which is incorporated by reference in its entirety to the extent not inconsistent with the disclosure herein.

BACKGROUND OF INVENTION

High-density arrays of oligonucleotide probes have been fabricated using spotting technology, spraying technology, electrostatic attraction, and high-resolution photolithography in combination with solid-phase oligonucleotide synthesis. Such forms of DNA detection technology, which are often associated with chip-based structures and microarrays, may be used for parallel DNA hybridisation analysis, directly yielding sequence information from genomic DNA fragments. Prior to sequence identification, the nucleic acid targets are commonly fluorescently labelled. This can occur prior to or after hybridisation to the oligonucleotide array, via direct chemical modification of the target strand or by use of an intercalant or groove-binding dye subsequent to hybridisation on the DNA microarray. The hybridisation pattern, as determined by fluorescence microscopy, is then deconvolved by appropriate chemometric processing to reveal the sequence of the target nucleic acid. Rather than focusing on selective detection of small quantities of a particular nucleic acid sequence as is done in the field of dedicated biosensors, this technology has focused on sequence analysis of nucleic acids in suitably high copy number so as to sufficiently occupy the oligonucleotide array.

Other spatially resolved approaches for development of microarray technologies have also been introduced where electrochemical manipulation of hybridisation at spots or pads of DNA can be done, and where the tips of fibres that form a fibre optic bundle are altered to house addressable discrete DNA microbeads. Further examples of spatially resolved devices include the use of spots of nucleic acids that are deposited onto a glass or fused silica surface by pin spotting or piezo-based ink jets, spatially resolved electrochemical analysis as found in Light-Addressable Potentiometric Analysis (LAPS) technology, and spatially resolved Surface Plasmon Resonance for pads that are located over conductive metals.

In all these cases, the concept is that individual independent spots, beads or pads of nucleic acid are deposited across a surface, and that the immobilized chemistry in each spot, bead or pad is consistent and discrete. In array technologies, each spot, bead or pad typically has a plurality of bound nucleic acid molecules and each spot, bead or pad can contain one or more, although typically a relatively small number of, different bound nucleic acids. The purpose of these arrays is to achieve detection of multiple targets, whether they be pathogenic organisms, mutations or combinations of genes that are concurrently up and down regulated. This is achieved in any one analysis by looking at alterations of a pattern of discrete signals on a surface. The approach is based on study of the results of many partially-selective reactions, where ideally the chemistry of each reaction can be defined and controlled. The problem with such approaches is that it is virtually impossible to select a stringency that is concurrently suitable for optimization of hybridisation at each and every spot, bead or pad, and the approach therefore incorporates a lack of selectivity by design. Furthermore, such detection devices are generally not amenable to providing absolute quantitative results and are not usually reusable.

Approaches to sensor development have basically taken two distinctive paths:

1) The use of one type of ssDNA sequence on a relatively large surface area for biosensor preparation.
2) The use of microarrays of many different ssDNA sequences, each different ssDNA sequence being immobilized in a small, discrete surface area, with many different ssDNA sites being distributed over a large surface area. (More recently, microarrays composed of discrete areas in which a relatively small number of different ss DNA are immobilized have been employed.)

Two common platforms used for development of DNA biosensors are Surface Plasmon Resonance Spectroscopy (SPR) and Total Internal Reflection Fluorescence Spectroscopy (TIRF). SPR can detect surface binding interactions in real time without the use of labels. SPR instrumentation is commercially available and Pharmacia's BIAcore™ instrument is in common use in many laboratories to investigate the kinetics of interfacial nucleic acid hybridisation, formation of triple-stranded complexes, to develop assays for selective detection of polymerase chain reaction (PCR) amplified nucleotides (N. Bianchi, C. Rutigliano, M. Tomassetti, G. Feriotto, F. Zorzato, and R. Gambari, *Clinical and Diagnostic Virology* 8, pp. 199–208, 1997) and to investigate the use of peptide nucleic acid (PNA) capture probes to enhance selectivity. The BIAcore system has been used by several groups for the monitoring of DNA-DNA interactions in real time (P. Nilsson, B. Persson, M. Uhlin, and P. Nygren, *Analytical Biochemistry* 224, pp. 400–408, 1995; M. Tosu, M. Gotoh, K. Saito, M. Shimizu, *Nucleic Acids Symposium Series* 31, pp. 121–122, 1994). The association and dissociation kinetics of target oligonucleotides composed of either complementary sequences or mismatched bases have been monitored. The authors claimed that differences in kinetic parameters could be detected for non-complementary strands as well as for various 20-mers containing two, four or six mismatched base pairs. The time required for each analysis was reported to be 15–20 minutes and the results showed promise for real-time interaction analysis for such processes as gene assembly, DNA polymerase activity, and sequencing experiments. Bier and Scheller (F. F. Bier and F. W. Scheller, *Biosensors and Bioelectronics* 11, pp. 669–674, 1996) used SPR to study the interaction of the restriction endonuclease EcoRE, a DNA modifying enzyme. The action of the enzyme was observed by measuring the loss of bound DNA after a short incubation with the enzyme.

Numerous evanescent wave fibre optic DNA sensors have been reported in the literature. The evanescent field typically penetrates about 200 nm to 400 nm (typically less than 1 µm) into the surrounding medium when using visible radiation, conferring surface selectivity (W. F. Love, L. J. Button, and R. E. Slovacek, in *Biosensors with Fibre Optics*. Eds. Wise and Wingard, pp. 139–180, The Humana Press Inc., 1991). The first such fibre optic DNA sensor was reported by Squirrell in 1992 (C. R. Graham, D. Leslie, and D. J. Squirrell, *Biosensors and Bioelectronics* 7, pp. 487–493, 1992). Preliminary experiments using covalently immobilised probe oligonucleotides and fluorescein-labelled complementary strands gave fast (60 second) detection in the nanomolar range with a linear response curve, but were not as sensitive as radio labelling techniques. Analysis of 204-base oligonucleotides showed that the detection of PCR products was feasible. Abel (A. P. Abel, M. G. Weller, G. L. Duveneck, M. Ehrat, and H. M. Widmer, *Analytical Chemistry* 68, pp. 2905–2912, 1996) operated a similar system in a competitive binding mode.

Sensitivity of evanescent biosensors may be significantly improved by use of mono-modal optical fibres (T. R. Glass, S. Lackie, and T. Hirschfeld, *Applied Optics*, 26, pp. 2181–2187, 1987). With use of mono-modal fibres, up to 10% of the optical power may be present in the evanescent field. Bier (F. Kleinjung, F. F. Bier, A. Warsinke, and F. W. Scheller, *Anal. Chimica Acta* 350, pp. 51–58, 1997), used two strategies for immobilisation of oligonucleotides to monomodal optical fibres: direct coupling to amino-activated surfaces or coupling via the avidin-biotin bridge. Using the fluorescent double-stranded ligands YOYO and picogreen, detection limits of 30 fM (3.2 amol) were achieved. These are the lowest detection limits reported to date for fibre optic DNA biosensors. The sensor was also able to detect single base pair mismatches in the target sequence.

A second major route to production of devices for DNA analysis involves placement of arrays of different sequences across surfaces, or at the tips of fibre-optic bundles (Michael, K. L., Taylor, L. C., Schultz, S. L., Walt, D. R., Anal. Chem. 1998, 70, 1242–1248). Automated oligonucleotide synthesis has seen commercial application by Fodor and Affymetrix (E. L. Sheldon, J. Briggs, R. Bryan, M. Cronin, M. Oval, G. McGall, E. Gentalen, C. G. Miyada, R. Masino, D. Modlin, A. Pease, D. Solas and S. P. A. Fodor, *Clinical Chemistry* 39, pp. 718–719, 1993; G. H. McGall, A. D. Barone, M. Diggelmann, S. P. A. Fodor, E. Gentalen and N. Ngo, *JACS* 119, pp. 5081–5090, 1997), where photolithography techniques have been used to grow arrays of oligonucleotides on DNA "chips". This involves the activation of glass surfaces and then extension of the surface with a hexaethyleneglycol-type linker. The terminal groups of the linker are blocked with photolabile protecting groups. These groups are then removed from predefined regions by selectively exposing the surface with light through photolithographic masks, followed by oligonucleotide addition. This has been done using phosphoramidites with photolabile protecting groups in the 5'-hydroxyl position, or more recently with conventional DMT protected phosphoramidites in combination with polymeric semiconductor photoresist films (G. McGall, J. Labadie, P. Brock, G. Wallraff, T. Nguyen, and W. Hinsberg, *PNAS*, 93, pp. 13555–13560, 1996). The phosphoramidites react only with the sites that were previously exposed to light. The process is repeated with different lithographic masks until the desired oligonucleotides are obtained. The number of oligonucleotide probes that can be immobilised is limited by the size of the chip and the lithographic resolution (M. Chee, R. Yang, E. Hubbell, A. Berno, X. C. Huang, D. Stem, J. Winkler, D. J. Lockhart, M. S. Morris and S. P. A. Fodor, *Science* 274, pp. 610–614, 1996). It has been reported that chips with 136,528 unique oligonucleotides have been synthesized on a 13 cm$^2$ chip.

Another approach involves placing aminated polypropylene sheets in a Southern Array Maker (SAM) and then standard phosphoramidite chemistry is applied to 64 distinct and independent channels producing 64 independent oligonucleotides (M. J. O'Donnell-Maloney and D. P. Little, *Genetic Analysis: Biomolecular Engineering* 13, pp. 151–157, 1996). Other methods involve a piezoelectric ink-jet dispenser that delivers discreet droplets of reagent to chip surfaces, or delivery by "printing" using bundles of capillaries or pins.

SUMMARY OF THE INVENTION

The present invention provides a very different approach to detection and quantitative measurement of nucleic acids, nucleic acid analogs, and agents that bind to or associate with nucleic acids or nucleic acid analogs, which uses spatially-resolved analysis of binding of such molecules to a surface carrying one or more spatially-distributed gradients of selectivity. In this approach, a surface carries one or more gradients of probe molecules wherein the gradient is formed by spatiality varying one or more physical, structural or functional properties of the probe molecules. For example, gradients of probe density (e.g., low to high density) and/or probe structure (e.g., sequence variation, different fictionalisation of probes) and/or the orientation of bound probes with respect to each other. The surface carrying the spatially-distributed gradient(s) is contacted with a sample to allow binding of targets in the sample to probes in the gradient. The surface is treated to remove non-selectively bound targets or optionally to adjust selectively of binding. Any spatially-resolved method is then employed to detect the selective binding of targets to the surface. The detection of patterns of binding to the one or more gradients allows the detection and identification of targets present in a sample. Additionally, detection of patterns of binding to the gradient as a function of contact time with the sample, or assay conditions including, among others, temperature, and washing conditions, e.g., salt concentration. Further, differential binding of different target molecules in a sample to the gradient can provide for separation of target molecules in a mixture.

In a specific exemplary embodiment this new method as applied to nucleic acid probe molecules is herein designated Gradient Resolved Information Platform (GRIP) which is based on a surface that is coated with an immobilized layer of nucleic acid molecules, which comprises at least one gradient of a varying physical, structural or functional property of the probe molecules. A surface can include one or more gradients of such properties, including, among others, gradients of probe density and/or probe sequence and/or probe orientation and/or probe structure. The methods are particularly useful with surfaces having one or more spatially-distributed gradients of single-stranded nucleic acid or single-stranded nucleic acid analog probe molecules.

The location, extent of binding or hybridisation, and speed of binding or hybridisation on such a surface by a target molecule is useful to isolate one or more targets and/or identify one or more bound targets and optionally to quantitatively measure the amount of one or more targets in a sample. The location and speed of signal development (e.g., of a label sensitive to binding or hybridisation) will be dependent on the stability of the hybrid or complex formed, which is in turn dependent on the density, sequence (or structure) and availability of the immobilized probes, e.g., single-stranded nucleic acid. Such an approach to detection adapts to alterations of the conditions of stringency (e.g., hybridisation or binding conditions), and nucleic acids or other target molecules in a mixture can each optimally bind at any one stringency by localizing to the area of highest energetic stabilization. Identification and quantification is based on the spatially resolved signal location and signal magnitude within any gradient. Many different device technologies that can spatially resolve a signal magnitude or rate of signal appearance can be used for detection of target binding.

The surfaces and substrates of this invention that carry one or more gradients of immobilized probe properties are useful in methods for the detection of one or more target molecules in a sample. Targets are detected by detecting their binding to the probe gradient. Spatially-resolved detection of target binding to determine the location in the gradient where the target binds facilitates identification of the bound target and quantitation of the amount of target (or relative amounts of targets) in a sample. The invention also provides kits for the detection of target molecules which comprise one or more substrates at least one of which substrates carries one or more gradients of immobilized probe which binds to the target.

More specifically, surfaces and substrates of this invention that carry one or more gradients of immobilised probe nucleic acids or nucleic acid analogues are useful in methods for the detection of one or more target nucleic acids that are at least in part complementary in sequence to a probe on the surface or substrate. Such surfaces and substrates are useful in hybridisation assays for detection of target nucleic acids in which the target binds to the gradient on surface or substrate. Spatially-resolved detection of target binding facilitates identification of the bound target and quantitation of the amount of target (or relative amounts of targets) in a sample. The invention also provides kits for the detection of target nucleic acids which comprise one or more substrates at least one of which substrates carries one or more gradients of immobilized nucleic acid probes which binds to a target.

In a specific example, fluorescent dyes that associate with the formation of double-stranded DNA (dsDNA) can be used to detect hybridisation of target nucleic acids to immobilized probe nucleic acids. Such dyes can be free in solution, can be associated with the target nucleic acid, or can be associated with single-stranded DNA (ssDNA) probe molecules on a surface. The intensity distribution of a pattern and the location of the pattern of the fluorescence upon hybridisation of immobilized probe molecules with target DNA can be used to identify and quantify one or more targets.

A further feature that can be included in the methods of this invention is immobilization of one or more references or markers, such as a known sequence of ssDNA in defined spatial zones on the gradient surfaces.

The new technology described herein provides for at least one and preferably a multi-dimensional distribution of selective chemistry at a surface, in such a way that the chemical coating layer on the surface operates to provide one or more gradients of selectivity in one or more directions on the surface. The coating layer or immobilization layer in which the gradient is formed is preferably continuous, but may be composed of discrete bands, spots or regions. A gradient is formed in a selected spatial distinguishable pattern on the surface, and preferably is formed along a dimension of the surface, e.g., along the length or width of a rectangular surface. Where two or more gradients are present the pattern of each gradient is distinct and identifiable. For example, two gradients on a rectangular surface are preferably formed in orthogonal directions or dimensions on the surface, e.g., along the length and width, respectively of a surface. In another example, a gradient can be formed with respect to a point on a surface or other geometric shape, e.g., varying as a function of radial distance from the point or varying linearly from a line on the surface. Any given surface may contain more than one gradient formed from more than one point, line and/or other geometric shape on the surface. For example, a radially varying gradient originating at a point on the surface may be combined with a linearly varying gradient originating from a line on (or an edge of) the surface.

The surfaces of this invention with one or more gradients of bound or immobilized probe molecules can be employed for the separation, isolation and/or detection and identification of one or more target molecules which can bind to probe molecules in a gradient on the surface.

The distributed chemistry on the surfaces of this invention provides the advantages that one or more target molecules in a sample can be separated by binding to different locations in the gradient on the surface; that a target molecule can be identified by determining the location of its binding within or on a gradient (by comparison to a known reference or marker, for example), and the quantity of the target molecule present in a sample can be determined by following signal magnitude in time(e.g., by detection of label as a function of time). Conventional spatially resolved imaging techniques (e.g. confocal microscopy, diode array, CCD, etc.), can be used in combination with the surface gradients of this invention to determine quantitative results with automatic correction for any changes of solution conditions (stringency). Various analytical techniques that offer spatially-resolved signal analysis can also be used (e.g. Surface plasmon resonance, electrochemistry, acoustic technologies, thermal analysis, surface enhanced Raman spectroscopy, surface potential measurement devices, mass spectrometry, fibre-optic bundles).

Other advantages of the invention include reversibility of chemistry, the ability to use tethered markers and/or mixed markers (for example, fluorescent dyes that preferentially associate with dsDNA), the use of calibration and referencing signals (e.g., the use of internal reference sequences and internal standards) that appear concurrently with the analytical signal.

In addition, the use of surface gradients is compatible with a variety of optical techniques, which allow the use of a waveguiding approach to improve signal generation and signal recovery (i.e. high sensitivity and low detection limit). The surfaces comprising gradients of probe molecules of this invention can function on many different device platforms, are suitable for concurrent assay of multiple nucleic acid targets, are suitable for determining the degree of selectivity to targets, and can operate in mixtures where there are multiple targets of differing lengths and where sample clean-up may not be complete.

The surfaces of this invention preferably have at least one substantially continuous gradient, wherein the average value of the parameter, upon which the gradient is based, is varied continuously in a defined pattern on a surface. Preferred surfaces of this invention contain at least one gradient of varying average density of bound probe molecules.

BRIEF DESCRIPTION OF THE DRAWINGS

FIG. 3A illustrates fluorescence from an ITO slide in which a continuous gradient formed by electrochemical hydroxylation, GOPS treatment (reflux in toluene), then washing with methanol, DCM, and ether (no immobilization of probe, no hybridisation to target, no label); FIG. 3B illustrates fluorescence from an ITO slide prepared as in FIG. 3A with immobilization of $dT_{20}$-$C_{12}$—$NH_2$ (0.05M-$H_2SO_4$) as in Example 2 followed by washing with sterile water; FIG. 3C illustrates fluorescence from an ITO slide in which a continuous gradient is formed by electrochemical hydroxylation, (with no treatment with GOPS), followed by immobilization of $dT_{20}$-$C_{12}$—$NH_2$ (0.05M-$H_2SO_4$) by spotting; and treatment with $dA_{20}$-$Cy_5$, followed by washing with PBS (No significant fluorescence is observed); FIG. 3D illustrates fluorescence from an ITO slide in which a continuous gradient is formed by electrochemical hydroxylation, followed by GOPS treatment (reflux in toluene), followed by immobilization of $dT_{20}$-$C_{12}$—$NH_2$ (0.05M-$H_2SO_4$) by spotting, followed by treatment with $dA_{20}$-$Cy_5$, and washing with PBS; FIG. 3E illustrates fluorescence from an ITO slide in which a continuous gradient is formed by GOPS treatment (neat with Hunig's base, 110° C., 60 min) after hydroxylation by plasma cleaning (15 min), followed by immobilization of $dT_{20}$-$C_{12}$—$NH_2$ (0.05M-$H_2SO_4$) by spotting; treatment with $dA_{20}$-$Cy_5$, and washing with PBS; FIG. 3F illustrates fluorescence from an ITO slide in which a continuous gradient is formed by homogeneous hydroxylation by the electrochemical method followed by treatment as for FIG. 3D; FIG. 3G illustrates fluorescence from an ITO slide in which a continuous gradient is formed by electrochemical hydroxylation, followed by treatment with GOPS (reflux in toluene), immobilization of $dT_{20}$-$C_{12}$—$NH_2$ (0.05M-$H_2SO_4$), followed by treatment with $dA_{20}$-$Cy_5$, and washing with PBS where DNA to be immobilized is not spotted, but spread along the slide; FIG. 3H illustrates fluorescence from an ITO slide in which a continuous gradient is prepared as for 3F, but only the upper half part (in red) is electrochemically homogeneously hydroxylated before GOPS treatment, immobilizing $dT_{20}$-$C_{12}$—$NH_2$ (0.05M-$H_2SO_4$) by spreading over entire surface; FIG. 3I illustrative results for hybridisation of partially complementary DNA $dT_8A_3T_9$-$Cy_5$, to immobilized $dT_{20}$, high contrast.

DETAILED DESCRIPTION OF THE INVENTION

Many microarray and biosensor platforms have been described to detect DNA hybridisation at interfaces. All of these approaches are predicated on the use of immobilised single-stranded nucleic acid (e.g., ssDNA) or a nucleic acid analog, and each is constrained by the physical chemistry of hybridisation in the environment defined by a surface. Thermodynamic considerations are often used to evaluate selectivity, and it is clear from this perspective that selectivity is not just a function of the nucleic acid sequence that is used to define a probe molecule. The thermodynamic stability of dsDNA is also dependent on nearest-neighbour interactions, e.g., between immobilized probes, including the extent of surface occupancy by ss nucleic acid and ds nucleic acid. This has consequences in terms of both selectivity and quantitative binding (equilibrium partitioning based on thermodynamic stability), and each can change as a result of the extent of formation of hybrids during an analytical experiment. Similar arguments apply for the kinetics of hybridisation and denaturation.

A fundamental issue is whether there can be confidence in assignment of sequence identification, and in quantitative analysis, when using markers (eg. fluorescent dyes, radiolabels, etc.) to detect the presence of dsDNA. Biosensors that are based on the use of one or a few sequences of ssDNA, or a device that is covered with many pads each containing one different ssDNA, cannot deal with the problems of selectivity and the thermodynamics of binding. At best, it might be possible to lay down a layer of ssDNA of known average density, and this can be used for calibration of concentration and selectivity over a narrow range of solution conditions and target DNA concentrations.

Figure 1:
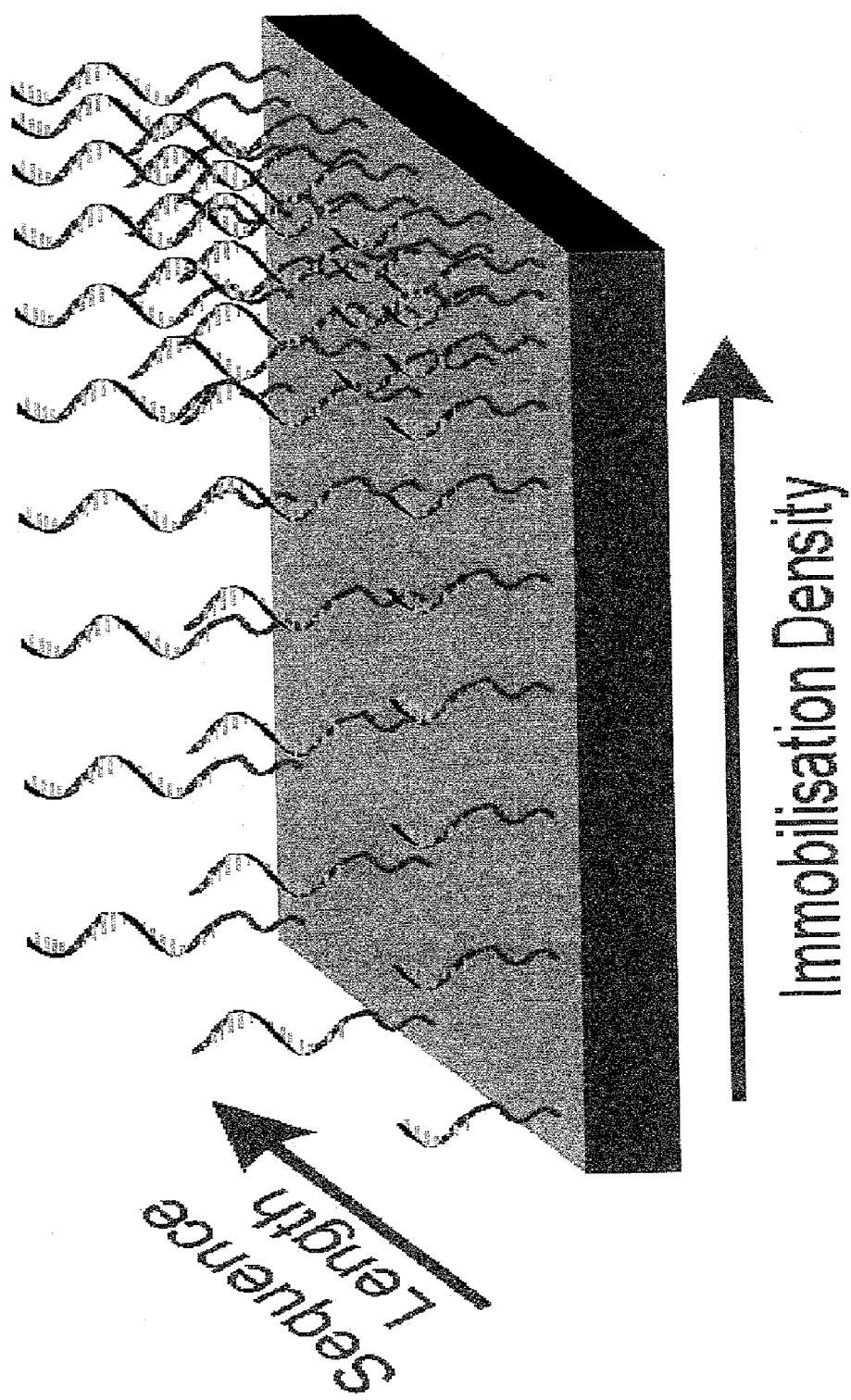
FIG. 1 is an illustration of a surface showing a two-dimensional gradient, where in one dimension the density of probe molecules is varied, and in the other dimension, the length of the immobilized sequence is varied.
Figure 2:
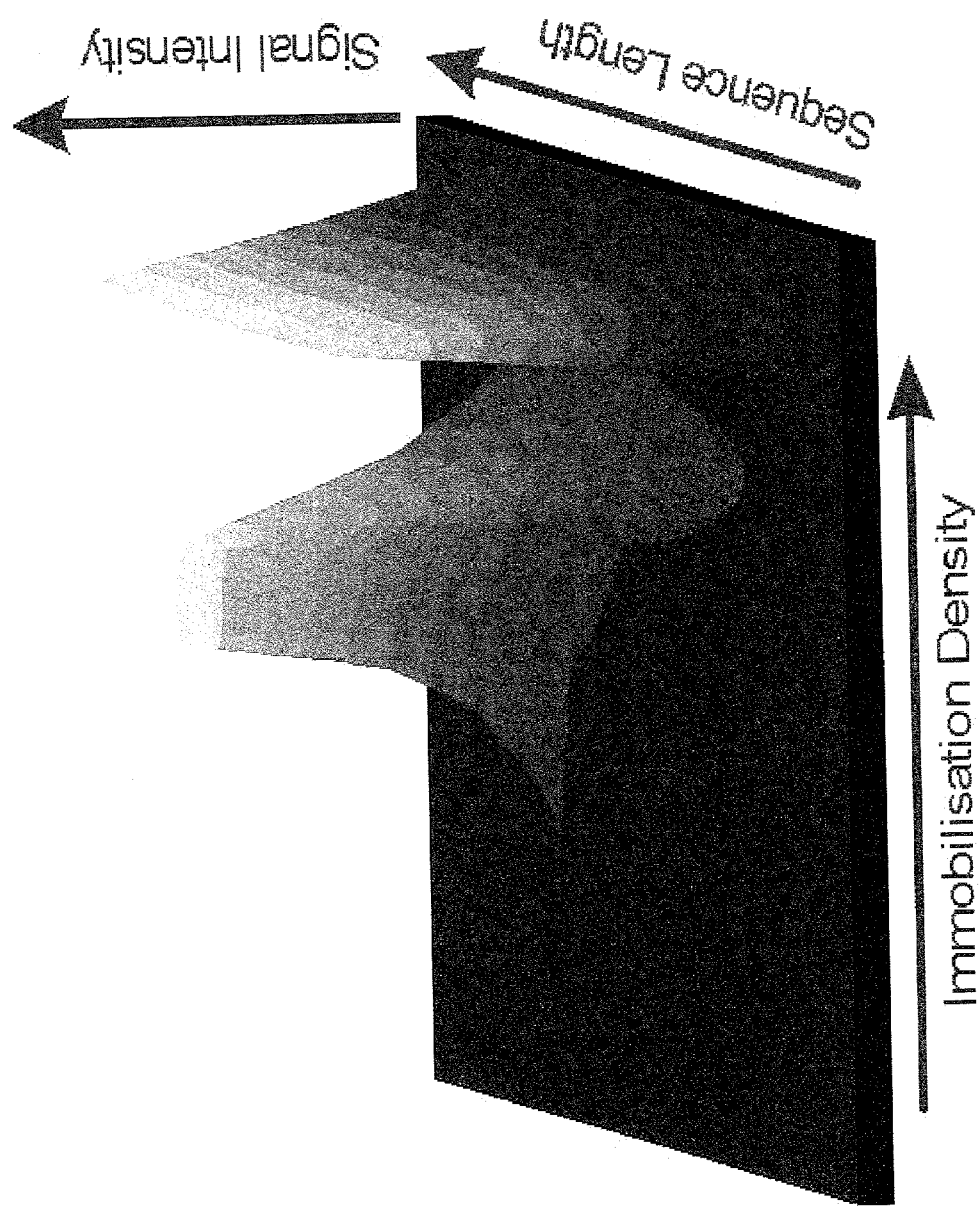
FIG. 2 illustrating a surface based on a two-dimensional gradient exemplifying the partitioning of a target (signal at left) into one zone, and a reference sequence onto a reference zone (signal at right).

A solution to this problem provided by this invention is based on a blend of concepts; the distributed chemistry approach as found in microarrays combined with the careful control of the spatial distribution of probe molecules on a surface. What can solve the aforementioned limitations is the device strategy of this invention that relies on the use of gradients of properties of the immobilized probe molecule which can affect target binding to probe, for example gradients of ssDNA density and sequence length as shown in FIG. 1. Such gradients can be grown on a substrate surface in a continuum across a device surface, with for example immobilized probe density varying in one dimension. Two or more gradients can be formed on a single surface, for example, with probe density varying in one dimension and sequence length varying in a second dimension. The result is a surface carrying one or more spatially-distributed gradients that will maximize thermodynamic stability of target binding in defined zones or bands. The binding pattern of targets can then be observed as a one- or multi-dimensional spatially resolved image with a signal intensity gradient profile, e. g., using fluorescence labelling, as shown in FIG. 2.

A reference zone can optionally be built along a surface. A reference standard can be added to the sample (internal standard), or can be built onto the surface (FIG. 2), so that the reference standard binds at the surface within a defined zone or band that can be easily identified and the signal measured quantitatively for comparison purposes. The location of binding and the signal magnitude of the reference standard serves to calibrate for environmental conditions of ionic strength, pH, temperature and even non-selective adsorption of interferents. A comparison of the reference signal to the analytical signal can be done by ratioing or other background correction techniques, and this provides for confidence in sequence assignment of a real sample as well as quantitative analysis.

The use of large surface areas and large area-to-volume ratios (sample volume) means that such surfaces can react very quickly for signal generation from target binding. Many signal transduction methods are well-known in the art and used in known assays which detect the selective binding of a probe molecule to a target molecule. These methods can be employed in the methods of this invention, and include, but are not limited to, detection of fluorescence from labelled target, fluorescent intercalators, fluorescent groove binders, molecular beacons, radioisotopes, surface potentials, coloured products, enzyme labelled targets, antibody labelled targets, and gold particle labelled targets.

In one embodiment of this invention, light emitted from fluorophores at a surface of a sensing device of this invention which carried one or more gradients can be monitored by a photomultiplier tube (PMT), a vidicon tube, a CCD or any other suitable one-dimensional scanning device or two- or multi-dimensional light detection equipment. In one specific application, the use of tethered fluorescent dyes permits fast, sensitive detection, and a regenerable device technology that can be used to measure multiple samples. Microscopy or waveguides can be used to collect fluorescence emission, followed by known chemometric methods for signal processing to discern patterns of binding from spatially resolved signals that are based on intensity, wavelength and time-resolved spectroscopy.

Gradients of probe molecule density (including mixtures of molecules such as ssDNA and other polyelectrolytes as spacers), sequence length, orientation and structure (eg. types of structures: aptamers, hairpins, lariats, and related structures) can be generated on surfaces by many different methods. As one example, a density gradient of hexaethyleneglycol (HEG) linker that is used as a template for subsequent immobilization of ssDNA is described herein. A gradient of density of HEG can be immobilized by allowing the HEG to react along different areas of a surface under suitable chemical conditions for different periods of time or at different concentrations. Control of reaction time can for example be achieved by controlling the speed of removal of a surface from a reactive HEG solution by dip-casting technology. Other techniques include gradient spraying or rolling, differential electrochemical reaction across a surface as can be done using a resistance drop, or any other means of controlling reaction time as a function of a dimension of the surface. Once the density gradient is established with a linker, automated nucleic acid synthesis, or single step oligonucleotide immobilization can then proceed to form a gradient of immobilized nucleic acid probes. A gradient density of reactive probe molecules can be immobilized to a surface in a manner similar to that described for HEG.

Another example that provides for a gradient of HEG is to immobilize a constant density of HEG that has a protecting group at the terminus, and then to remove the protecting group as a gradient across the surface. This creation of a gradient of capped HEG insures that further coupling of probe molecules is controlled spatially, as the probe molecules can only be immobilized at uncapped HEG linkers.

Another example of a parameter that can be varied to create a gradient of selectivity is sequence length of probe molecules. For example, this can be achieved by use of enzyme assembly of segments of nucleic acid, or by enzymatic disassembly of oligonucleotides, using an approach that controls reaction time. This control can be achieved using dip-casting methodology, spraying, rolling, and other methods.

Another parameter that can provide a gradient of selectivity is the orientation of immobilized probe molecules. The orientation of probe molecules can be controlled by density manipulation, and by selection of nucleotide sequences so that folding and bending can be induced in the probe structure.

A further example of a parameter that can provide a gradient of selectivity is the distribution of formal surface charge or dielectric constant. For example, charged linker molecules (with carboxymethyl or amine moieties), or a mixture of charged and uncharged linker molecules, can be deposited on a surface as a gradient using controlled dip casting methods, gradient spraying or rolling as discussed above. The gradient of electrostatic fields influences the alignment and mobility of probe molecules that are subsequently immobilized, and can affect the thermodynamic stability and kinetics of formation and dissociation of probe-target hybrids.

Another alternative is to generate a gradient of reporter molecules or markers that can report the presence of hybridisation as a function of location in the gradient, for example, a gradient of tethered intercalating dyes can be generated on a surface using methods which control the rate of the tethering reaction.

The surfaces that can be used to support gradients of nucleic acids or nucleic acid analogs are many, and include, but are not limited to, fused silica, quartz, silicon, plastics, glass, gold, metals, transparent electrodes (e.g., indium tin oxide or related materials), ceramics (e.g., metal oxides), paper, conductive carbon, and conductive polymers. Immobilization of the nucleic acids and nucleic acid analogs or other probe molecules can be achieved by covalent bonding, adsorption, biotin-avidin linkage, thiol-gold interactions and any other method that can attach the materials at a controllable density, sequence length or orientation. The surface may be of any shape convenient for conducting spatially resolved imaging or detection. Gradients may be formed as a function of any dimension of the substrate, e.g., along a length or a width of a substrate, extending radially from a point on a surface or extending linearly from a straight line on a surface.

Gradients can be achieved by templating the surface with activation sites or linkers for attachment of nucleic acids and nucleic acid analogs, and by controlling the sequence length, sequence type, and orientation of probes, across a surface. Methods of preparation of gradients include but are not limited to use of controlled dip-casting and use of controlled reaction time, generation of gradients of light intensity in a photocatalyzed immobilization, generation of mechanical gradients achieved by spraying and/or rolling, control of capping reagents and cap densities, control of sequence length by annealing of segments of nucleic acids, and removal of portions of sequences by degradation methods.

While not necessary, it is possible to immobilize probe molecules onto a linker or spacer. In such a case, the length of the spacer between the substrate and the first nucleoside is chosen to be sufficiently long so that the environment of the terminal nucleoside is fluid enough to permit efficient coupling with oligonucleotides, or successive nucleotide monomers during automated phosphoramidite synthesis of the immobilized nucleic acid probe. This is in accord with the report of Beaucage et al (1992, Tetrahedron, 48: 2223–2311) wherein it was stated that substrate linkers of lengths of at least 25 atoms are required to achieve high (>99.5%) synthon coupling yields in automated nucleic acid synthesis. Because the linker is terminated by a protected nucleoside, any reactive sites on the support that would lead to the production of unwanted side products during automated synthesis can be eliminated by treating the derivatised supports with a surface-capping agent such as acetic anhydride prior to synthesis. Using such an approach, a gradient of capping on a surface can be created by controlling the time of reaction along the surface.

An amine-terminated solid support suitable for automated oligonucleotide synthesis may be prepared according to the method of Brennan et al (1993, Sensors and Actuators B 11 109). A functional amphiphilic support derivatisation agent is created by condensing aminopropyltriethoxysilane (APTES) with 12-nitrododecanoic acid. Similarly, a surface can be activated with other reagents such as glycidoxypropyltrimethoxysilane (GOPS) according to the method of Watterson et al. (2000, Langmuir, 16: 4984). This yields a substrate derivatised with short spacer molecules with terminal epoxide moieties. The support may then be capped using standard methods employed during automated synthesis (acetic anhydride), or with chlorotrimethylsilane (R. T. Pon *Methods in Molecular Biology*, Vol. 20: Protocols for Oligonucleotides and Analogs, S. Agrawa., Ed., 1993, Humana Press, Inc. Totowa N.J.), thereby masking other sites of reaction which may produce unwanted side products during oligonucleotide synthesis. The length of the spacer arm is then extended by nucleophilic attack of a polyether, such as hexaethylene glycol (HEG), in an acid catalyzed expoxide ring-opening reaction, yielding a stable ether linkage (U. Maskos and E. M. Southern, 1992 *Nucl. Acids Res.*, 20(7). 1679). Polyether chains provide for hydration, flexibility for molecular motion, and improved biocompatibility in terms of minimization of non-selective binding to biological compounds. This support is then used directly for oligonucleotide attachment by automated synthesis wherein an ammonolysis resistant phosphoramidite linkage is made between the activated support and the first nucleotide, or for direct immobilization of a oligonucleotide. Analogous to the natural internucleotidic linkage, a phosphodiester linkage between the substrate linker and first nucleotide is completely resistant to ammonolysis under the conditions which remove standard base-protecting groups.

Since polyethylene glycols are bifunctional, there exists the possibility of creating non-reactive closed-loop structures that may significantly decrease the amount of loading of oligonucleotides on the surface of an optical fibre. To eliminate any such problem, one terminus of the polyether can be protected with a suitable blocking group, for example, with a dimethoxytrityl (DMT) functionality, prior to extension of the glycidoxypropyltrimethoxysilane. In the case where a chromophoric protecting group is used (such as DMT), an additional advantage is provided wherein facile determination of the amount of support linkers may be determined by monitoring the absorbance of the deprotection solution (e.g. 504 nm for DMT+).

Mono-dimethoxytrityl protected polyethylene glycols may be introduced onto the surface by a number of methods. Surfaces that are first functionalized with GOPS, as in the method of Maskos and Southern, may then be treated with a solution of mono-dimethoxytritylated polyethylene glycol over sodium hydride to afford linkage of the polyether to the terminal epoxide moiety of the immobilized GOPS via a base catalyzed epoxide ring-opening reaction. Mono-dimethoxytritylated polyethylene glycols (such as DMT-HEG) can also be directly linked to the surface by activation of the terminal hydroxyl moiety of the polyether with methane sulfonyl chloride or beta-cyanoethyl-N,N-diisopropylphosphitylchloride. In the later case, the polyether substrate linker is attached as a phosphoramidite synthon that can be done as part of the automated oligonucleotide synthesis procedure, thereby making the entire fabrication protocol completely automated following cleaning of the substrate surfaces.

In exemplary embodiments, the probe molecules to be bound onto the terminus of the substrate linker (or directly onto an activated substrate surface) can include immobilized nucleic acids (DNA and RNA), modified nucleic acids, and nucleic acid analogs prepared by well-known methods or by straight-forward extension or modification of those methods. The term nucleic acid includes polynucleotides, oligomers, and doubled-stranded polynucleotides. There is no specific size limit on nucleic acids used for immobilization in this invention. However, problems due to self-hybridisation and reduced selectivity may occur with longer nucleic acids. As used herein, the term "nucleic acid analogs" includes modified nucleic acids. As used herein, the term "nucleotide analog" includes nucleic acids where the internucleotide phosphodiester bond of DNA or RNA is modified to enhance bio-stability of the oligomer and "tune" the selectivity/specificity for target molecules (Ulhmann, et al, 1990, Angew. Chem. Int. Ed. Eng., 90: 543; Goodchild, 1990, J. Bioconjugate Chem., 1:165; Englisch et al, 1991, Angew, Chem. Int. Ed. Eng., 30: 613). Such modifications may include and are not limited to phosphorothioates, phosphorodithioates, phosphotriesters, phosphoramidates or methylphosphonates. RNA may be assembled on a surface or prepared separately and linked to the support by post-synthesis reactions. RNA monomers are commercially available, as are some 2'-O-modified synthons. The 2'-O-methyl, allyl and 2'-deoxy-2'-fluoro RNA analogs, when incorporated into an oligomer show increased biostability and stabilization of the RNA/DNA duplex (Lesnik et al., 1993, Biochemistry, 32: 7832). As used herein, the term "nucleic acid analogs" also include alpha anomers, L-DNA (mirror image DNA), 2'-5' linked RNA, branched DNA/RNA or chimeras of natural DNA or RNA and the above-modified nucleic acids. Back-bone replaced nucleic acid analogs can also be adapted for in the present invention. For purposes of the present invention, the peptide nucleic acids (PNAs) (Nielsen et al, 1993, Anti-Cancer Drug Design, 8: 53; Engels et al, 1992, Angew, Chem. Int. Ed. Eng., 31: 1008) and carbamate-bridged morpholino-type oligonucleotide analogs (Burger, D. R., 1993, J. Clinical Immunoassay, L6: 224; Uhlmann, et al., 1993, Methods in Molecular Biology, 20,. "Protocols for Oligonucleotides and Analogs," ed. Sudhir Agarwal, Humana Press, NJ, U.S.A., pp. 335–389) are also embraced by the term "nucleic acid analog." Both exhibit sequence-specific binding to DNA with the resulting duplexes being more thermally stable than the natural DNA/DNA duplex. Other backbone replaced nucleic acids are well-known to those skilled in the art and may also be used in the present invention (See e.g., Uhlmann et al 1993, Methods in Molecular Biology, LO, "Protocols for Oligonucleotides and Analogs, Ed. Sudhir Agrawal, Humana Press, NJ, U.S.A., pp. 335).

In the present invention, nucleic acid sequences are attached to the surface. In one embodiment, an automated DNA synthesizer is used to grow nucleotide oligomers onto the surface, particularly an activated fused silica or glass surface, via the well-established β-cyanoethylphosphoramidite method. Any commercially available automated DNA synthesizer can be used.

Control of immobilization of probe molecules can also be achieved by reactions that immobilize such molecules in one step. For example, oligonucleotides can be immobilized in one step by reaction of one terminus of a strand with an active site on a surface, but high density of coverage with probe molecules is more difficult to achieve. Free strands of nucleic acids can be covalently attached directly or via linker molecules. This approach allows the use of DNA or RNA isolated from natural sources, amplified nucleic acids or their analogs, or synthetic samples provided in the fully deprotected form. Protocols provide end-attached oligomers of a well-defined orientation. Chemically stable linkages between the support and oligonucleotide may be employed to enhance the robustness of the surface. For example, surfaces derivatised with linker molecules terminated with either hydroxyl or amino groups can serve as substrates for carbodiimide-mediated coupling with terminally phosphorylated single-stranded nucleic acids. Coupling to hydroxyl groups produces a phosphodiester bond while coupling to an amine yields a phosphoramidate bond. Oligonucleotides can be phosphorylated, in solution, either chemically via a modification of Ouchi's method (Sowa et al Bull. Chem. Soc., Japan 1975 48 2084) or enzymatically.

Covalent attachment of free short strands of single-stranded nucleic acids can be achieved by a slight modification of the method Ghosh and Musso (Ghosh and Musso, 1987, Nucleic Acids Res. 15: 5353). Coupling of a 5-aminohexyl derivatised oligomer with activated carboxyl fibres affords end-attached oligomers. This method is known to minimize reaction at the amino groups of the DNA bases (which would potentially compromise the hybridisation event) and affords surfaces with excellent nucleic acid coverage. The synthesis of the 5'- or 3'-terminally modified oligomers can be achieved readily by standard methods (Ghosh and Musso, 1987; Beaucage and Iyer, 1993).

Contrary to the conventional preparation of oligonucleotides on controlled pore glass, post-synthesis removal of the product from the support is not desired. In order to prevent cleavage of the oligonucleotide from the support while removing the protecting groups of the nucleobases, two modifications to the usual synthetic protocol can be made. The approach involves the combination of a hydrolysis resistant linkage between the oligomer and support along with the use of labile base protecting groups. Thus, an oligomer of any sequence can be prepared and deprotected, yet remain attached to the support, available for hybridisation.

Substrates such as planar wafers, curved surfaces, and optical fibres and waveguides, may be used in the present invention. One embodiment utilizes optical waveguides. Optical waveguides are advantageous as optical supports due to their small size, high light transmission capability, and ability to allow total internal reflection (TIR) of light. Waveguides may operate by the evanescent wave or direct excitation methods, and the direct excitation mode can achieve detection limits better than $10^6$ molecules (PCT/CA98/00402; WO98/58079).

One example of a detection system is based on a glass or fused silica wafer that is coated with one or more gradients of probe molecules, where hybridisation is detected by fluorescence. In such an experiment, a side-on extrinsic mode of light collection approach is typically used for investigations carried out on planar supports. The surface is illuminated by a light source located approximately normal to the surface and fluorescence emission is also monitored by equipment placed approximately normal to the surface. In another embodiment, an intrinsic mode arrangement is used to monitor fluorescence emission from the surface of optical waveguides. Light is transmitted through the waveguide that supports the nucleic acid coating on its surface. Excitation by total internal reflection or direct excitation causes emission of fluorescence, and emission is also monitored by detection equipment placed approximately normal to the surface.

Fluorescence is one analytical method that is preferentially chosen for the transduction of hybridisation events into a measurable analytical signal. Fluorescence techniques have long been known to provide high sensitivity (comparable to radioisotopic methods) and detailed information about structure at the molecular level (Lakowicz, 1983, Principles of Fluorescence Spectroscopy. Plenum Press, NY). Changes in the polarity, pH, temperature, microviscosity, or orientation of molecules in the local environment of a fluorophore may result in alteration of the electronic structure or collisional probabilities of the fluorophore. Such environmental changes may be detected by monitoring fluorescent signal parameters such as intensity, wavelength, lifetime, or polarization. For example, it is not uncommon for the efficiency of fluorescence emission (quantum yield) and fluorescence lifetime of an intercalant fluorophore to increase by an order of magnitude or more when inserted into the rigid and hydrophobic base stacking region of double-stranded nucleic acids with respect to that of the unbound dye in solution.

One example of the present invention utilizes, but is not limited to, the fluorescence intensity response of fluorophore that is associated with dsDNA via monitoring in a spatially resolved configuration along the surface to quantify the location and presence of hybridized nucleic acids at the surface. The fluorescence intensity is related to the amount of target nucleic acid or nucleic acid analog initially present in solution. The time dependence of the rate of change of the fluorescence intensity increase upon hybridisation can be measured to determine the concentration of target nucleic acid, or time-resolved fluorescence methods can be used to detect the location of target molecules, and to measure signal intensity.

In one embodiment of this invention, the fluorophore can be any one of a large number of compounds that selectively bind with hybridized target in comparison to the probe molecule. One example of a common intercalating agent is ethidium bromide (EB). The ethidium cation (3,8-diamino-6-phenyl-5-ethyl-phenanthridium) is a fluorescent compound which strongly associates with double-stranded nucleic acids by intercalation into the base-stacking region and, in some cases, the major groove of the double helical structure (Monaco et al., 1993, Journal of Bimolecular Structure and Dynamics, 10: 675).

In another embodiment of this invention, the fluorophore or reporter group may be attached to the 5'- or 3'-end of the oligomer by a tether such as a hydrocarbon, polyether, mixed aliphatic, aromatic, peptidic or oligonucleotide chain. The tether need not be restricted to the 3'- or 5'-ends of the oligomer, but may be attached to a terminal or internal ribo-residue via the 2-hydroxyl (Yamana et al, 1991, Tetrahedron Letters, 32: 6347). Similarly, a tether can be attached to a terminal or internal nucleobase using pyrimidines (Pieles et al, 1990, Nucleic Acids Research 18: 4355) or purines (Roduit et al, 1987, Nucleosides and Nucleotides 6: 349). Furthermore, the internucleotidic linkage can be a site for tether attachment (Agrawal et al, 1990, Nucleic Acids Research 18 5419). It will be appreciated by those of ordinary skill in the art that any combination of these methods can be used to incorporate multiple reporter groups at specific sites. An example of a tethered fluorophore is an ethidium analogue with a $C_{13}$ acid tether, that is attached to 5'-hexylamine functionalized oligonucleotides immobilized on the surface of an optical fibre to generate the biosensor with the tethered fluorophore probe (Krull, Piunno, Wust, Li, Gee and Cohen, Proc. of NATO ARW on Biosensors for Direct Monitoring of Environmental Pollutants in Field, Kluwer Acad. Pub., ASI Series 2, 38: 67–77, 1997).

Thompson and Krull ({a} M. Thompson and U. J. Krull, *Trends in Analytical Chemistry*, 3 (1984) 173–178. {b} M. Thompson and U. J. Krull, *Analytical Chemistry*, 63 (1991) 393A–405A) teach that biosensors may be defined as reversible devices which consist of a biorecognition element and a transduction element. The biorecognition element may be a biological material capable of participating in highly selective binding to a target, usually a biologically significant molecule. The transduction element converts the selective binding reaction into a measurable analytical signal. The transduction strategy of the GRIP technology can be designed so that the devices are classified as a biosensor, whereas microarray systems generally do not contain a transduction element at all.

For example, by associating the transduction element, which can be a tethered dye, with the biorecognition element, the GRIP technology of this invention functions without the need for external reagent treatment and eliminates the need to collect and dispose of hazardous waste. Such a technology readily lends itself to automated and in-line analysis and precludes the need for skilled technicians to partake in the analysis procedure or disposal of waste (provided the sample itself is not biohazardous). Another advantage provided by the incorporated dye is internal calibration. More specifically, three key advantages may be realized: 1) the associated dye provides a means to determine the quantity of fluorophore and immobilized nucleic acid anywhere on the surface; 2) the fluorophore in the presence of single-stranded nucleic acid provides a baseline signal to which all signals can be referenced, hence providing meaningful analytical data; and 3) the useful lifetime of the device can be determined from alterations in the background fluorescence signal from the incorporated fluorophore over time. Once the signal drops below some specified level (that indicates there has been undesirable photobleaching), then the surface would be replaced. Therefore, by including a tethered marker that can transduce hybridisation, an internal reference and diagnostic tool for the device status can be included as an integral part of the optical biosensor.

The choice of fluorophores which may be used in solution, or be attached to or be tethered to the oligonucleotide include organic intercalating complexes, such as the commonly used nucleic acid stain ethidium bromide, thiazole orange and analogs thereof as prepared by L. G. Lee et al (1986, Cytometry Z: 508) and the YOYO, BOBO, and TOTO series of cyanine based intercalant fluorophores which are commercially available from Molecular Probes Inc. (Eugene, Oreg.). Inorganic coordination complexes, such as the "molecular light switch" Ru (phen)$_2$ dppz PF$_6$ developed by Jenkins et al. (1992, J. Amer. Chem. Soc. 114: 8736) may also be used as well as groove binding dyes, such as Hoechst 33258 and Hoechst 33342, which are commercially available from Aldrich Chemical Co. (Milwaukee, Wis.). These fluorophores are chosen such that the fluorescent probe is quenched (non-emissive) when in the presence of single-stranded nucleic acids and provides intense luminescence when in the presence of double-stranded nucleic acids. This change in observed luminescence occurs via changes in the relative rates of radiative and non-radiative relaxation processes of the probe when the external environment changes from aqueous solution to a hydrophobic and highly structured one in the base-stacking region of double-stranded nucleic acids. Other examples of classes of fluorophores which can be used in the present invention include but are not limited to, acridine dyes, phenanthides, phenazines, phenothiazines, quinolines, alfatoxin, polycyclic hydrocarbons, oxirane derivatives, actinomyces, anthracyclinones, thiaxanthenones, anthramycin, mitomycin, platinum complexes, polyintercalators, norphilin-A, fluorenes and fluorenones, furocoumarins, benzodipyrones and monostral fast blue. Preferred dyes are also those that provide large Stoke's shifts, can be excited at long wavelengths and have large differences in fluorescence lifetime, quantum efficiency, and/or wavelength of excitation and emission when in solution as compared to when bound to hybridized nucleic acids.

One example of an instrument used for fluorescence intensity measurements is based on an epi-fluorescence microscope (eg. Brennan et al 1990, Anal, Chim. Acta., 237: 253, modified to observe surfaces). The sensing surface is situated within in a small volume, stop-flow, hybridisation chamber made of a suitable inert material with good thermal conductivity (e.g. stainless steel or titanium). The temperature of the hybridisation may be controlled by use of a suitable thermoelectric housing to provide rapid thermostating to the desired temperature and computer control. The temperature of the solutions in the hybridisation cell may be accurately determined (within 0.2° C.) by use of a glass-encapsulated thermistor incorporated into the hybridisation cell. Solution delivery to the hybridisation cell and sensing surface may be done by use of a computer-controlled pump (e.g. peristaltic pump) where all solutions originate from a computer-controlled autosampler. Fluorescence emission from fluorophores associated with immobilized nucleic acid complexes can be directed towards an interference filter with the appropriate bandpass window to select for the emission of the fluorophore. Fluorescence radiation traversing the interference filter then enters a video camera, and the image is processed to determine spatial distribution of intensity, where intensity provides a quantitative measure of the target sequence and background interference.

In alternative embodiments, the radiation source can be a frequency-doubled laser, a semiconductor laser, bright lamp or LED. Coupling can occur into a waveguide, and can be accomplished with fibre couplers. Regeneration of the surface can be achieved by thermal methods such as by elevating the temperature within the flow-through hybridisation cell or by chaotropic methods in which solutions of highly polarized salts alter the hydrogen bonding structure of the solution to affect denaturation of the hybridized complex. In either case, the stability of hybridised material in the system is reduced to the point where hybridisation is not energetically favourable and the complement strands are dissociated from the covalently immobilized oligomers and may be flushed out of the flow cell. Regeneration methods as described herein can be employed to recycle biosensors.

Formation of multi-stranded nucleic acids (i.e. nucleic acid complexes composed of 3 or more strands), such as triplex nucleic acids, may be determined (A. H. Uddin, P. A. E. Piunno, R. H. E. Hudson, M. J. Damha and U. J. Krull, *Nucleic Acids Res.* 25, pp. 4139–4146, 1997). For example, normally, the fluorescence efficiency of a fluorophore increases with decreasing temperature owing to reduced collisional deactivation as a consequence of the reduced kinetic energy of the molecules surrounding the fluorophore. Fluorescence efficiencies with negative temperature coefficients are readily observed for fluorophores in solution as well as for fluorophores intercalated into nucleic acids. When multi-strand formation occurs, (e.g. binding of a third strand in the major groove of a double-helical nucleic acid) exclusion of the bound ligand often follows as the partition coefficient for the fluorophore in the multi-stranded nucleic acid is often much reduced with respect to that of the same fluorophore in double-stranded nucleic acid. The ligand exclusion process will also show a temperature dependence where reduced ligand binding is observed as the temperature of the system is decreased. As such, a positive temperature coefficient of fluorescence intensity would be observed for fluorophores associated with multi-stranded nucleic acids as increasing amounts of fluorophore become excluded from the highly-structured environment within the nucleic acid complex into bulk solution where the probability for collisional quenching of fluorescence is far greater. A net positive temperature coefficient of fluorescence intensity would then be observed for a fluorescent nucleic acid binding ligand in a multi-stranded nucleic acid. The temperature at which multi-strand formation occurs could also be assayed from the maxima in a fluorescence intensity versus temperature plot where the temperature coefficient changes from negative (for the dye bound in double-stranded nucleic acid) to positive (for the dye being excluded from the multi-stranded nucleic acid complex), as reported by Uddin and Piunno (Uddin, Piunno, Hudson, Damha and Krull, Nucleic Acids Res., 25: 4139–4146, 1997).

The methods of this invention can provide for rapid clinical testing for viruses (e.g., HIV, T cell lymphotropic virus 1 and 2, hepatitis B and C), pathogenic bacteria (e.g.

*E. coli.*, Salmonella, Listeria, Chlamydia ssp., *Trichomonas vaginalls, Gradenerella vaginids*) as well as other microorganisms (eg., fungi such as *C. albicans*) and organisms (eg., Cryptosporidia, Giardia). Genetic alterations can be detected (e.g., genetically modified foods). Detection and measurement of genetic disorders (e.g., cystic fibrosis and sickle-cell anemia) and diseases such as cancer can also be accomplished by the methods and apparatus of the present invention. The methods and apparatus of this invention can also be used to identify potential therapeutics to treat such diseases (e.g. branched antisense nucleic acids which inhibit expression of targeted nucleic acid sequences via triplex formation with that particular sequence, effectively shielding the genetic information from being read by transcription enzymes). The methods and apparatus of this invention can further be used in determination of the association of compounds with nucleic acids or nucleic acid analogs, as would be of interest in screening of potential agents that could serve as drugs.

In specific embodiments, the invention relates to the use of substrates carrying at least one gradient of immobilised probe density for the isolation, detection or quantitation of one or more target molecules that bind or hybridise to the probe molecules in the gradient. Immobilisation density refers to the average separation of neighbouring immobilised species (e.g., molecules), including probes, directly or through a linker to a surface. A gradient can be formed on a given surface by immobilization of probes alone or by immobilization of various mixture of probes and non-binding spacer molecules, e.g., co-immobilised oligomers that are not probes, which do not bind to targets. Density of immobilisation relates to the extent of physical interactions that can occur among neighbouring immobilized species and when only probes are immobilized density relates to the extent of physical interactions that can occur among neighbouring probes. A gradient of probe density refers to a spatially distributed variation of density of immobilise probes or mixtures of probes and spacer molecules (i.e., a change of density as a function of location on a surface). Typically, the gradient of density will increase or decrease in a selected spatial pattern, e.g., density increasing along a slide from bottom to top or side to side. More specifically, in specific probe density gradients, density will increase from a low density to a high density. When immobilisation density is low immobilized species, including probe molecules, are sufficiently separated such that no physical interactions can occur between neighbouring species. When immobilisation density is high, immobilised species, including probes, are sufficiently close that significant interaction between neighbouring species is probable. Immobilization density can be measured as the average mean separation of species on a surface.

Qualitative definitions of immobilization density depend not only on absolute number density of immobilized species, e.g., immobilized probes and any other co-immobilized species, such as non-nucleic acid oligomers, but also on the average dimensions of the immobilised species. Consequently, low immobilisation density is represented by the case where the ratio ($r_s$) of the mean center-to-center separation distance between neighbouring immobilized species to the average length of the immobilised species is significantly greater than two. High immobilisation density is represented by the case where the ratio ($r_s$) as defined above is less than or equal to about 1.7. It will be appreciated by those of ordinary skill in the art that the length of an immobilised species calculated based on the structure of the species and any linker to which it may be attached is an estimate of the space on the substrate surface that can be occupied by the immobilised species. Immobilised oligomers may occupy a larger area than expected based on their length due to the effect of molecular shape or orientation, the effect of extended solvent structure (e.g., hydration), the effect of the electrostatic field of the immobilised species and the like.

Substrates and surfaces of this invention can be employed in hybridisation assays to detect the presence of target nucleic acids that bind to immobilised probes. Assay conditions including those conditions that affect the stringency of hybridisation that are employed in standard hybridisation assays, e.g., temperature, ionic strength (e.g., salt concentration), can be readily adapted for use with the substrates and surfaces of this invention, as illustrated in the examples herein.

This invention also provides kits for conducting assays for the detection and/or quantitation of one or more target molecules in sample which comprise a surface of this invention carrying at least one gradient of probe properties that affect binding to a target molecule. The kit can further comprise reagents for carrying out the assay, including labels, hybridisation buffers, washing solutions and the like. A kit may further contain instructions for carrying out the assay. Reagents in the kit can be provided in discrete pre-measured amounts appropriate for conducting a selected number of assays. Alternatively, a kit of this invention can comprises reagents for making a desired gradient of probe molecules and optionally instructions for making the gradient desired.

The invention is further illustrated and exemplified by the following non-limiting examples.

EXAMPLES

Example 1

Probe Density Gradients on Fused Silica Optical Wafers

Immobilized single-stranded DNA (ssDNA) is used as a selective probe molecule to bind complementary and partially complementary nucleic acids. The density of ssDNA on a surface determines nearest neighbour interactions, surface interactions and charge density due to ionizable phosphate groups. This results in a local ionic strength, pH and dielectric constant at the surface that is substantially different from that in bulk electrolyte solution. It is the local conditions that influence the thermodynamics of hybridisation, and this is manipulated by temperature control as related to the melt temperature ($T_m$, which is defined as the temperature at which half of all duplexes originally formed are denatured into the single-stranded state), of double-stranded DNA (dsDNA). Organosilane chemistry is used to covalently immobilize hexaethylene glycol (HEG) linkers to the surface and to control the subsequent density of $dT_{20}$ that is prepared by automated synthesis.

Biosensors based on fused silica optical wafers are coated with DNA and are used to distinguish duplexes of mixtures of fluorescein-labelled and unlabeled $dA_{20}$ and $d(A_9GA_{10})$ having a single base mismatch. Each thermal denaturation of dsDNA at the surface of the optical wafers is accompanied by a 2–3 fold reduction in standard enthalpy change, relative to values determined for denaturation in bulk solution. The experimental results demonstrate that the thermodynamic stability of duplexes that are immobilized on a surface is dependent on the distribution of density of immobilized DNA. The deviation in $T_m$ arising as a result of the presence of a centrally located single base-pair mismatch is significantly different at different densities of ssDNA, and the results demonstrate that surface density of DNA can be tuned to design analytical figures of merit.

Methods for control of nucleic acid density on surfaces are also described in U.S. patent application Ser. No. 09/993,303, filed Nov. 21, 2001 which is incorporated by reference herein in its entirety.

Experimental

Materials

Solvents are obtained from BDH (Toronto, ON) as reagent grade and are further purified or dried, when necessary, by standard distillation methods. Reagent grade salts are purchased from BDH (Toronto, ON). DNA synthesis reagents are from Dalton Chemical Laboratories Inc. (Toronto, ON.). Anhydrous acetonitrile (Dalton) is dried by distillation from $P_2O_5$ prior to receipt, and is further distilled from calcium hydride under a dry argon atmosphere prior to use. Tetrahydrofuran (BDH) is first dried over $CaH_2$, filtered and finally distilled immediately prior to use from sodium metal (Aldrich)/benzophenone (Aldrich). Sterile water for use on its own and with hybridisation buffer is produced with the water first double-distilled in glass, then subsequently treated with diethyl pyrocarbonate (Aldrich) and sterilized by autoclave. Molecular biology grade polyacrylamide gel electrophoresis reagents and apparatus are obtained from Bio-Rad (Hercules, Calif.). Silica gel (Toronto Research Chemicals, Toronto, ON) that is used for purification has a particle size of 30–70 microns.

Preparation of Optical Wafers

Fused silica optical wafers are cleaned prior to modification of the surface according to the two-stage method of Kern and Puotinen (W. Kern and D. A. Puotinen, RCA Rev., v.6. p. 187, 1970). The first stage consists of immersing the solid substrates in a 1:1:5 (v/v) solution of 30% ammonium hydroxide/30% hydrogen peroxide/water and gently agitating at 80° C. for five minutes. In the second stage, the substrates are recovered, thoroughly washed with sterile water and then gently agitated in a solution of 1:1:5 (v/v) conc. HCl/30% hydrogen peroxide/water for five minutes at 80° C. The substrates are then recovered and washed with successive 100 ml portions of water, methanol, dichloromethane and diethyl ether. The substrates are then dried under vacuum and stored in-vacuo and over $P_2O_5$ until required.

Surface Modification of Solid Substrates:

Functionalization of Substrates with 3-Glycidoxypropyltrimethoxysilane (GOPS)

The cleaned solid substrates (fused silica wafers) are suspended in an anhydrous solution of xylene/3-glycidoxypropyltrimethoxysilane/diisopropylethylamine (100:30:1 v/v/v). The reaction takes place at 80° C. with stirring. Substrates are left over a period of 24 hours under an argon atmosphere if one density of GOPS is desired (in an alternative method, they are slowly withdrawn by a mechanical lift from the reaction solution over a period of up to 24 hours). The substrates are then collected and successively washed with two 50 ml portions of each of methanol, dichloromethane, diethyl ether, and are dried and stored under vacuum and over $P_2O_5$ at room temperature until required.

Linkage of DMT-HEG onto GOPS Functionalized Substrates

DMT-HEG (dimethoxytrityl hexaethylene glycol) is synthesized as outlined previously (R. T. Pon in S. Agrawal, "Methods in Molecular Biology: Protocols for Oligonucleotides and Analogs", Vol. 20, Humana Press Inc., Totowa, p. 465, 1993; B. Sojka, P. A. E. Piunno, C. C. Wust and U. J. Krull, Anal. Chim. Acta., v. 395, p. 273, 1999). DMT-HEG (700 mg DMT-HEG/100 mg CPG) is dried under vacuum and over $P_2O_5$ (>72 hrs.) and is dissolved in 20 ml of anhydrous pyridine. An excess of NaH (10 eq.) that has been thoroughly washed with dry hexane is then introduced to the mixture. The subsequent reaction is permitted to proceed with stirring for 1 hour at room temperature under an argon atmosphere. The reaction mixture is filtered through a sintered glass frit under a positive pressure of argon into a vessel containing the GOPS functionalized substrates. The substrates then undergo the DMT-HEG coupling reaction, which is permitted to proceed under a positive pressure of argon at room temperature with gentle agitation on an oscillating platform stirrer. Substrates are first fully immersed. Substrates coated with one density of GOPS are further prepared by slowly withdrawing the wafer by a mechanical lift over the period of the reaction of up to 12 hours to produce a gradient of immobilized HEG (for substrates that have varying coating densities of GOPS, these are allowed to activate by complete immersion for periods of 1, 4 and 12 hours to create gradients of HEG density). Following the coupling reaction, the substrates are quickly recovered and washed with successive 150 ml portions of methanol, water, methanol, and diethyl ether to quench the coupling reaction and remove any reactants that are non-specifically adsorbed. The DMT-protected HEG-functionalized substrates are dried under vacuum and over $P_2O_5$ and are maintained under these conditions until further required. In a further modification of this method, substrates can be exposed to a number of cycles of exposure to HEG to build up a higher density of HEG (Sojka, Piunno, Wust, and Krull, Appl. Biochem. Biotechnol., 89: 85–103, 2000).

Capping of Unreacted Silanol and Hydroxyl Functionalities with Chlorotrimethylsilane (TMS-Cl)

Unreacted silanol and hydroxyl functionalities on the surface of the solid substrates where undesired oligonucleotide synthesis can occur are capped prior to oligonucleotide synthesis using TMS-Cl according to the method of Pon et al (R. T. Pon in S. Agrawal, "Methods in Molecular Biology: Protocols for Oligonucleotides and Analogs", Vol. 20, Humana Press Inc., Totowa, p. 465, 1993). The dried substrates are suspended in a solution of 1:10 (v/v) chlorotrimethylsilane/pyridine for 16 hrs under an argon atmosphere at room temperature. The substrates are subsequently recovered and washed with three successive 20 ml portions of pyridine, methanol and diethyl ether and are then stored under vacuum and over $P_2O_5$ at room temperature until required.

Solid Phase Phosphoramidite Synthesis of Oligonucleotides

All solid phase oligonucleotide synthesis is done using a PE-ABI 391-EP DNA synthesizer (Perkin-Elmer Applied Biosystems, Foster City, Calif., USA). The pre-programmed synthesis cycles employed for oligonucleotide assembly are modified to adjust the reagent delivery times in order to ensure that the synthesis columns used are completely filled. The column used for oligonucleotide synthesis onto wafers is a custom manufactured Teflon® synthesis column. All end-caps are secured onto the column bodies with aluminium crimp seals. Synthesis of oligonucleotides for use as complementary material for immobilized DNA is carried out on nucleoside functionalized LCAA-CPG substrates pre-packed in polyethylene columns as supplied by the manufacturer. Detritylation is done using 3% trichloroacetic acid in dichloromethane or 2% dichloroacetic acid in dichloromethane. Activation of phosphoramidites for synthesis onto substrates is achieved with 0.5M tetrazole in acetonitrile (LCAA-CPG substrates) or ethylthiotetrazole (DMT-HEG-CPG substrates). Reagents for acetylation of unreacted hydroxyl functionalities are prepared as follows: Cap A, 10% acetic anhydride and 10% collidine in THF; and Cap B, 16% N-methylimidazole in THF (w/v). Oxidation is done with a solution of iodine, 0.1M, in THF/pyridine/water (25:20:2, v/v/v). Prior to oligonucleotide synthesis, the derivatised solid-supports are treated with the acetylating reagents by completing the capping portion of a standard synthesis cycle, to ensure blocking of any remaining hydroxyl functionalities. Phosphoramidite reagents are dissolved in dry, freshly distilled acetonitrile to a concentration of 0.1 M. Polythymidylic acid icosanucleotides ($dT_{20}$) are assembled onto all of the optical wafers and CPG substrates functionalized with DMT-HEG linker molecules. Determination of the density of surface coverage of CPG substrates with covalently immobilized oligonucleotide-HEG conjugates is done by anion-exchange HPLC (Sojka, Piunno, Wust and Krull, Anal. Chim. Acta, 395: 273–284, 1999).

Icosanucleotides labelled at the 5'-terminus with a fluorescein moiety are used as complementary material to hybridize with immobilized $dT_{20}$ sequences. The 5'-fluorescein labelled oligonucleotides are prepared by use of a fluorescein phosphoramidite synthon (Dalton) and standard protocols for oligonucleotide preparation. Additionally, unlabeled complementary icosanucleotides are prepared by standard protocols for use in studies of hybridisation in bulk solution.

Instrumentation for Studies of Immobilized Nucleic Acids

Fluorescence-based studies of nucleic acid hybridisation at the surface of optical wafers are carried out using a fluorescence microscope. Laser radiation (488 mn) from a Coherent Innova 70 CW argon ion laser (Coherent Laser Products, Palo Alto, Calif.) is incident upon the surface of a dichroic mirror (505 nm cut-off, Omega Optical, Battleboro, Vt., USA) oriented at 45° to the incident beam. The optical wafer is illuminated with the laser radiation. Fluorescence emission from the sensing wafer with wavelength greater than 505 nm is then directed back through the dichroic mirror into a Dage (Michigan City) semiconductor intensified target imaging camera. Images are captured and are processed to measure the intensity of fluorescence emission across the surface of the wafer. Instruments that are designed for microarray applications such as the Virtek Vision, Inc. ChipReader can be used to study surfaces for distribution of fluorescent materials.

Thermal Denaturation

All fluorescence intensity profiles for hybridisation occurring at the surface of the optical wafers are acquired by monitoring the intensity of fluorescence emission at 542 nm at a defined temperature, and the temperature is either scanned or is set in the range of ca. 20–80° C. All sensors are cleaned by sonication in ethanol in a 40W bath sonicator for 90 minutes to remove adsorbed impurities from the sensor surface prior to analysis. Thermal denaturation profiles are obtained for surfaces that are exposed to mixtures of $dA_{20}$ and $dA_{20}$-5'-fluorescein in a 100:1 molar ratio, and $d(A_9GA_{10})$ and $d(A_9GA_{10})$-5'-fluorescein (100:1 molar ratio) in various dilutions of a stock phosphate buffered saline (PBS) hybridisation buffer (1.0 M NaCl, 50 mM $PO_4^{-n}$, pH 7.0). Dilutions of the stock buffer by factors of 1.0, 0.5 and 0.1 are used for ionic strength studies. All analyses are done in triplicate for each ionic strength of PBS buffer investigated, and the standard deviation in $T_m$ values is less than 2° C. for each sample set. Removal of complementary oligonucleotide associated with the surface from previous analyses is done prior to each subsequent experiment by flushing with 80° C. water, and by flushing with 90% formamide in TE Buffer (10 mM Tris-HCl, 5 mM EDTA, pH 8.3).

Immobilization Density Considerations

The immobilization of polythymidylic icosanucleotides ($dT_{20}$) onto the substrates is achieved by means of a modification to the method of Maskos and Southern (Maskos, U and Southern, E. (1992) Nucleic Acids Res. 20(7):1679–1684; Maskos, U and Southern, E. (1993) Nucleic Acids Res. 21(20):4663–4669). The fused silica substrates are first functionalized with glycidoxypropyltrimethoxysilane (GOPS). Hexaethylene glycol (HEG), protected on one terminus with dimethoxytrityl (DMT) in order to ensure single-site reactivity and to minimize the risk of formation of closed-ring structures, is then covalently attached to the epoxysilane layer. The modified substrates are then subjected to standard cyanoethyl-phosphoramidite oligonucleotide synthesis protocols to prepare by stepwise synthesis the $dT_{20}$ oligonucleotides on the surface of the substrates.

In this example, the density of oligonucleotide immobilization is controlled by means of controlling a templating reaction. A gradient of HEG can be used to establish a gradient of DNA density. The gradient of HEG is controlled by the reaction time of DMT-HEG conjugates with the GOPS-functionalized substrates. Ultimately, a gradient of DNA is immobilized along the length of the surface of a 2 cm wafer. It is possible to identify areas of different densities of DNA on a wafer. For example, it is possible to locate where the DMT-HEG coupling reaction proceeds for 1, 4 and 12 hours. In order to characterize the density of immobilization, oligonucleotide synthesis is carried out as described above on GOPS-functionalized controlled-pore glass (CPG), which has a well-defined surface area. The oligonucleotide-HEG conjugates are cleaved from the surface of the CPG by means of exposure to concentrated ammonium hydroxide for approximately three hours, lyophilized and re-dissolved in water. The immobilization densities at specific times of reaction, as well as the quality of automated synthesis of all immobilized oligonucleotide samples, are subsequently analyzed by anion-exchange HPLC. Quantification of the cleaved HEG-$dT_{20}$ conjugates is achieved by co-injection with a known quantity of $dT_{20}$. The results of the HPLC analysis are shown in Table 1 for particular times of reaction.

Table 1 shows a selection of three discrete densities that are considered in thermal denaturation experiments. This selection is made so that comparison of three different physical environments for the immobilized oligonucleotides can be done. The low-density zone on the wafer consists of immobilized $dT_{20}$-HEG conjugates separated by approximately 370 Å between adjacent strands, assuming uniform oligonucleotide distribution. Since the length of the $dT_{20}$-HEG conjugate is ca. 100 Å in length, the low-density sample represents the system wherein there is, on average, very little chance of interactions between neighbouring strands that may affect hybridisation. The medium-density zone consists of immobilized $dT_{20}$-HEG conjugates separated by approximately 170 Å between adjacent strands, which may permit the onset of some interaction between neighbouring strands. Finally, the high-density zone consists of immobilized $dT_{20}$-HEG conjugates separated by approximately 52 Å between adjacent strands. This close packing is much more likely to facilitate interactions between neighbouring strands than the lower packing densities.

TABLE 1

Density of Immobilization of $dT_{20}$-HEG Conjugate onto GOPS-Functionalized Substrates as Determined by Anion-Exchange High Performance Liquid Chromatography

| Sample | Reaction Duration (DMT-HEG-Substrate) (Hrs.) | Total Surface Area of CPG Used (Å$^2$) | Molecules $dT_{20}$-HEG Immobilized | Average Radius per Molecule (Å) |
|---|---|---|---|---|
| Low Density | 1 | $2.62 \times 10^{19}$ | $2.41 \times 10^{14}$ | 185 |
| Medium Density | 4 | $2.62 \times 10^{19}$ | $1.15 \times 10^{15}$ | 85 |
| High Density | 12 | $4.12 \times 10^{19}$ | $1.90 \times 10^{16}$ | 26 |

Thermal Denaturation of Surface Immobilized Oligonucleotide Hybrids

Wafers that are prepared by synthesizing $dT_{20}$-HEG conjugates onto the surface of functionalized fused silica are subjected to hybridisation and thermal denaturation experiments. Complementary oligonucleotide solutions contain mixtures of unlabeled $dA_{20}$ and $dA_{20}$-5'-Fluorescein, together in a 100:1 molar ratio, with a total oligonucleotide concentration of $10^{-7}$ M. It is assumed that the fluorescein label would not seriously impede the hybridisation process, and a control thermal denaturation experiment is conducted in bulk solution using $dA_{20}$-5'-Fluorescein and $dT_{20}$ as the complementary oligonucleotides (0.5×PBS, 0.62 μM dsDNA, equimolar in each strand). The observed $T_m$ is 55±1° C., which is in reasonable agreement with that observed in an analogous experiment using unlabeled $dA_{20}$ (54±1° C.).

Similarly, studies of hybridisation thermodynamics of sequences containing a centrally located SBPM (single base pair mismatch) are done using analagous mixtures of unlabeled and labelled $d(A_9GA_{10})$ in the same molar ratio and with the same total oligonucleotide concentration. Complementary oligonucleotides are introduced into hybridisation buffers of various ionic strengths (0.1, 0.3, 0.5 or 1 M NaCl) to establish the trends in interfacial hybridisation thermodynamics as they relate to the ionic strength of the hybridisation solution.

The $T_m$ data observed at the different zones of the wafer with the specified oligonucleotide packing density in hybridisation buffers of different ionic strengths and using $dA_{20}/dA_{20}$-fluorescein as the complementary material is reported in Table 2.

TABLE 2

Observed $T_m$ (° C.) values for Different Zones on Wafer Surface Using Hybridisation Buffers of Various Ionic Strengths and $dA_{20}/dA_{20}$-5'-fluorescein as the Complementary Material

| [NaCl] (M) | Low Packing Density $T_m$ (° C.) | Medium Packing Density $T_m$ (° C.) | High Packing Density $T_m$ (° C.) |
|---|---|---|---|
| 0.1 | 40 | 42 | 32 |
| 0.5 | 50 | 48 | 43 |
| 1.0 | 55 | 53 | 46 |
| $\partial T_m/\partial \log[Na^+]$ (° C.) | 15 | 11 | 14 |

The data in Table 2 illustrate the effect of packing density on the thermodynamics of hybridisation. The high packing density facilitated some destabilization of the hybridized immobilized oligonucleotides as evidenced by the $T_m$ values which were consistently lower than those observed with the low packing density and medium packing density.

In order to establish trends in the hybridisation energetics which govern selectivity, thermal denaturation experiments identical to those described above are done using $d(A_9GA_{10})/d(A_9GA_{10})$-fluorescein as the complementary material. The observed $T_m$ values at the various zones of packing density are listed in Table 3.

TABLE 3

Observed $T_m$ (° C.) values for Different Zones of Biosensors Using Hybridisation Buffers of Various Ionic Strengths and $d(A_9GA_{10})/d(A_9GA_{10})$-fluorescein as the Complementary Material

| [NaCl] (M) | Low Packing Density $T_m$ (° C.) | Medium Packing Density $T_m$ (° C.) | High Packing Density $T_m$ (° C.) |
|---|---|---|---|
| 0.3 | 39 | 39 | 31 |
| 0.5 | 42 | 42 | 33 |
| 1.0 | 48 | 46 | 37 |
| $\partial Tm/\partial \log[Na^+]$ (° C.) | 18 | 13 | 10 |

Examination of the data in Tables 2 and 3 shows that in the zones with low and medium oligonucleotide packing density, the deviations in $T_m$ caused by the presence of a centrally located SBPM are larger when hybridisation occurs in solutions of lower ionic strength, relative to those observed in experiments done in hybridisation buffers of higher ionic strength. The results indicate that the opposite trend was observed from the zone of high oligonucleotide packing density. It appears that the higher packing density of immobilized DNA permits greater interaction between neighbouring strands under conditions of increased ionic strength within the hybridisation solution and the immobilized nucleic acid layer. This would result in greater destabilization of the Watson-Crick bonding within the hybrids and would lead to greater deviations in the observed $T_m$ for solutions of higher ionic strength.

The results indicate that the different zones of density (and therefore anywhere along the gradient of density across the surface of the wafer) provide for differing selectivity of any one target sequence. A target sequence optimally (energetically) binds to the gradient at some particular zone (see FIG.

2) that is defined by temperature, ionic strength, pH and density of nucleic acid. Comparison of two related sequences that differ by a single base pair mismatch shows that at any one temperature, pH and ionic strength, the location of the zone of binding alters as a function of density of nucleic acid that is immobilized. A change of temperature, ionic strength, or a gradient of temperature applied along a surface, results in shift of the position of the optimal binding condition. These results demonstrate that the use of a surface carrying at least one density gradient of nucleic acid probes in hybridisation assays can allow identification of a target sequence and distinguish between different target sequences. The use of one or more reference channels on one wafer carrying a probe density gradient or two or more identical wafers carrying density gradients at different environmental conditions, improves the ability to distinguish different sequences. The location, intensity and speed of development of intensity of zones of binding are used to distinguish between different nucleic acid sequences, and the intensity at the zone is used to measure the quantity of target that has hybridized.

Selectivity coefficients for a given nucleic acid hybridisation experiment are estimated by computing the ratio of the fraction of single-stranded DNA ($f_{ss}$) from fully complementary hybrids to that from the partially complementary hybrids at a given temperature, T. These values are obtained directly from thermal denaturation profiles. In the cases examined here, the selectivity coefficients are calculated as follows:

$$KA_{20}/A_9GA_{10}(T) = \frac{1 - fss, A_{20}(T)}{1 - fss, A_9GA_{10}(T)} \quad (1)$$

The computed values for the selectivity coefficients of hybridisation of $dA_{20}$-5'-fluorescein relative to $d(A_9GA_{10})$-5'-fluorescein for zones representing low, medium and high $dT_{20}$ immobilization density as well as those for analogous experiments done in bulk solution are shown in Table 4.

that observed in a bulk solution environment. Furthermore, the data show that selectivity of hybridisation does not necessarily follow the trend of $T_m$ that is seen as a function of ionic strength and oligonucleotide immobilization density. There is an ensemble of interactions that will occur along with the hybridisation-denaturation transition in an interfacial environment. These interactions contribute to the overall stability of binding of target DNA to probes, and therefore play an important role in defining the $T_m$ values of a particular probe-target complex, and the selectivity of hybridisation in different spatial zones on a surface.

Consequences of Competitive Hybridisation to Analysis

An important consideration in the evaluation of the sensitivity and selectivity of hybridisation for a given sensor system is the nature of the sample being introduced. Samples may contain various levels of protein, and large non-complementary genomic DNA and RNA molecules that may interfere with analysis. Also, most nucleic acid sensor systems will be exposed to the target DNA of interest in double-stranded form. This imposes the requirement of denaturing these double-stranded targets so that selective hybridisation may subsequently take place at the sensor surface. In practice, this may result in a competition for hybridisation of target strands in bulk solution between immobilized probe oligonucleotides, and the complementary DNA in bulk solution. This competition for selective hybridisation may impart some significant limitations on the sensitivity and selectivity of the assay. To better understand the effects of competitive hybridisation between surface immobilized hybrids and those that form in bulk solution, the values of the fraction of double-stranded DNA are determined directly from normalized thermal denaturation profiles as follows:

$$f_{ds}(T) = 1 - f_{ss}(T) \quad (2)$$

The values of $f_{ds}$ are shown in Table 5 for different temperatures, ionic strengths, and zones of immobilization densities, where $dA_{20}$-5'-fluorescein was used as the

TABLE 4

Selectivity coefficients of hybridisation of $dA_{20}$-5'-fluorescein relative to $d(A_9GA_{10})$-5'-fluorescein at zones of different $dT_{20}$ density on a surface, and for an analagous system in bulk solution, at various temperatures and ionic strengths.

| | Selectivity Coefficient, $k_{A20/A9GA10}$ | | | | | | | |
|---|---|---|---|---|---|---|---|---|
| Temp (° C.) | Low Density 1 × PBS | Low Density 0.5 × PBS | Medium Density 1 × PBS | Medium Density 0.5 × PBS | High Density 1 × PBS | High Density 0.5 × PBS | Bulk Solution 1 × PBS | Bulk Solution 0.5 × PBS |
| 30 | 1.0 | 1.0 | 1.0 | 1.0 | 1.0 | 1.00 | 1.0 | 1.0 |
| 40 | 1.0 | 1.1 | 1.0 | 1.5 | 2.6 | 5.4 | 1.0 | 1.0 |
| 50 | 2.4 | 84.9 | 2.7 | 7.3 | 6.6 | 14.5 | 1.7 | 4.3 |
| 55 | 42.1 | 15.5 | 44.4 | 6.0 | 11.1 | 0.0 | 7.5 | 61.4 |
| 60 | 12.6 | 0.0 | 17.1 | 0.0 | 0.0 | 0.0 | 15.3 | 0.0 |

The data in Table 4 show that the selectivity of hybridisation in an interfacial environment, such as on a surface, is substantially different and advantageous in comparison to complementary material for interfacial hybridisation experiments, and $dA_{20}:dT_{20}$ hybrids were examined in bulk solution.

TABLE 5

Fraction of double-stranded DNA at various temperatures and ionic strengths, at zones of different $dT_{20}$ immobilization densities using 0.1 uM $dA_{20}$-5'-fluorescein as the complemetary material, and for an analagous system in bulk solution (0.6 uM $dA_{20}$:$dT_{20}$).

| | Fraction of Double-stranded DNA, $f_{ds}$ | | | | | | | |
|---|---|---|---|---|---|---|---|---|
| Temp (° C.) | Low Density 1 × PBS | Low Density 0.5 × PBS | Medium Density 1 × PBS | Medium Density 0.5 × PBS | High Density 1 × PBS | High Density 0.5 × PBS | Bulk Solution 1 × PBS | Bulk Solution 0.5 × PBS |
| 30 | 0.99 | 1.00 | 1.00 | 1.00 | 0.98 | 1.00 | 1.00 | 1.00 |
| 40 | 0.99 | 1.00 | 1.00 | 0.99 | 0.82 | 0.70 | 1.00 | 1.00 |
| 50 | 0.78 | 0.56 | 0.77 | 0.39 | 0.28 | 0.18 | 0.99 | 0.87 |
| 55 | 0.44 | 0.16 | 0.44 | 0.10 | 0.00 | 0.00 | 0.83 | 0.31 |
| 60 | 0.13 | 0.01 | 0.12 | 0.00 | 0.00 | 0.00 | 0.21 | 0.00 |

The significance of the term $f_{ds}$ becomes apparent when considering the mechanism of signal development in fluorescence-based sensors where fluorescent dye that associates with the dsDNA structure is used to detect formation of duplexes. The dyes are commonly intercalators or groove binders, but in either case are selected to bind to dsDNA and not ssDNA. The parameter $f_{ds}$ therefore defines the maximum amount of dsDNA that can be stained to achieve detection. Considering the results presented in Tables 4 and 5, it can be concluded that a balance can be struck between the desired sensitivity and selectivity of a given hybridisation assay, and this balance is continuously tunable by means of controlling a gradient of density of ssDNA on the surface in combination with controlling environmental parameters such as ionic strength and temperature.

Example 2

Preparation of Gradients on ITO Substrates

Materials

Aqueous ammonia (30%), dichloroacetic acid, dichloromethane (DCM), diethylether, acetone, methanol, iodine, toluene, tetrahydrofuran (THF), pyridine were purchased from BDH (Toronto, ON, Canada). N, N-diisopropylethylamine (Hunig's base), 1-methylimidazole, 3-glycidoxypropyltrimethoxysilane (GOPS) from Aldrich. All phosphoramidite reagents, pre-packed columns, pre-prepared capping agents, 0.45M-tetrazole solution (activator), and DNA synthesis grade acetonitrile were from Dalton Chemical Laboratories (Toronto, ON, Canada). Indium-Tin Oxide (ITO) slides ($In_2(Sn)O_x$, 50×7×0.7 mm, passivated, unpolished float glass cuvette, coated one side slides, $R_s \leq 20$ Ω) were from Delta Technologies (Stillwater, Minn., USA). 5'-Amino-modifier $C_{12}$ was from Bio/Can Scientific (Mississauga, Ont, Canada). $Cy_5$-Amidite (dye Amidite 667) was from Pharmacia (Bare D'urse, QC, Canada).

Solvents were dried under an inert atmosphere of dry argon (Canox, Bramalea, ON, Canada). Toluene was dried over sodium metal in the presence of benzophenone. Acetonitrile and DCM were dried over calcium hydride. Water was purified by a Milli-Q-five stage cartridge purification system, Millipore (Mississauga, ON, Canada). Sterile water was prepared using glass double-distilled water that was autoclaved at 121° C. for 20 min.

All oligonucleotides were synthesized using ABI 392 DNA synthesizer of Applied Biosystems (Foster City, Calif., USA). Linker deposition (phosphoramidite-$C_{12}$—$NH_2$) was done in a similar manner. Preparation of reagents for oligonucleotides synthesis was followed by the literature method. (B. Sojka, P. A. E. Piunno, C. C. Wust, U. J. Krull, Analytica Chim. Acta., 395, 1999, 273, and references therein)

Linker DNA, $dT_{20}$-$C_{12}$—$NH_2$ was prepared from a synthesis support dT-column, dT-phosphoamidite and phosphoramidite-$C_{12}$—$NH_2$. Linker DNA, $dA_{20}$-$C_{12}$—$NH_2$ was prepared similarly using a corresponding column and reagents. Fluorescenct DNA, $dA_{20}$-$Cy_5$, $dT_{20}$-$Cy_5$ and $dT_8A_3T_9$-$Cy_5$ ($Cy_5$ is cyanine 5) were obtained from the reaction of synthesis support $dA_{20}$-column, $dT_{20}$-column and $dT_8A_3T_9$-column, respectively, with phosphoramidite-$Cy_5$ (20 µmol, 0.2 mL of 0.1 M, each) in 0.45 M-tetrazole (0.2 mL each) activator solution under argon in a glove bag, followed by the treatment of the columns with an oxidizing agent solution (1 mL of 0.1 M-$I_2$ each in THF/pyridine/water, 160/40/4 mL). The de-protection process was accomplished using an ammonia solution (30%) at room temperature for 24 hours for labelled-DNA, and at 47° C. for 15 hrs for the linker DNA. All DNA was purified by Polyacrylamide Gel Electrophoresis (PAGE) and de-salted using NAP-10 columns.

ITO (indium tin oxide) slides were marked and labelled on the surfaces of the coated side using a sharp tungsten needle with a voltage applied. The slides were then washed using a sonicator (Branson 1510) in a dilute liquid soap solution, continuously with warm water, methanol for 30 min each, and dried in an oven overnight prior to use.

Hydroxylation of ITO (Indium tin oxide) slides

Electrochemical hydroxylation using Versa Stat from EG&G (Princeton Applied Research) was done by chronoamperometery at −0.85 V with a platinum counter electrode, a silver/silver chloride reference electrode, and an ITO slide as a working electrode in 0.5M-$H_2SO_4$. ITO slides are treated in the following ways to create gradients of coverage of hydroxyl groups.

Continuous gradient: Silver and platinum electrodes are dipped into 10 mL of 0.5 M-$H_2SO_4$ solution in a 100 mL beaker. A dried ITO slide is placed in the beaker in such a manner that about 5 mm of the lower end is dipped into the solution and about 5 mm of the upper end is held tightly with the alligator clip of the working electrode positioned vertically so that the slide is perpendicular to the surface of the solution. Above the beaker is placed a 200 mL cylindrical separatory funnel, filled with 0.5M-$H_2SO_4$. The stopcock of the funnel is adjusted prior to placement of the glassware to release the acid solution gently to the beaker at a flow rate of 3.5 mL/sec. The funnel outlet tip is placed against the inner wall of the beaker to avoid a dropwise addition. The solution in the funnel is released to the beaker gently without disturbing the surface of the solution in the beaker immediately after an electric current is applied to the system. The current is applied for 35 sec. The slide is remover from the beaker and washed with double distilled water several times, then dried in an oven (120° C.) at least for one day.

Stepwise gradients: Electrodes and 0.5M-$H_2SO_4$ solution are prepared and placed similarly as above for Continuous Gradients. A small area of the lower part (ca. 4 mm) of an ITO slide is dipped into the solution along with the other electrodes. An electric current is applied to the system for 3.5 sec. To the solution is added about 8 to 9 mL of the acid solution from the funnel so that another 4 mm of the lower part of the slide is immersed into the solution. Current is applied to the system for 3.5 sec as before. The same process is repeated until the slide is completely immersed in the solution. The total time count is 3.5 sec times ten. The upper area of 4 mm is exposed to an electric current for about 3.5 sec while the bottom 4 mm, is exposed for 35 sec. In order to avoid a leakage of electric current, the slide in solution should not touch the inner wet wall of the beaker, nor should the alligator clip touch the surface of the solution during the last step of the process. The slide is then washed and dried similarly as described above.

Hydroxylation is also done using an atmospheric pressure plasma cleaner (PDC-32G, Harrick Scientific, Ossining, N.Y., USA). Samples are inserted into the cleaner, and are activated by exposure for different times to the plasma using atmospheric gas at reduced pressure.

Reaction with GOPS

General method: Two dry slides and a magnetic stirring bar are placed in a very dry 250 mL round bottom flask filled with argon. To this is added 66 mL of freshly dried toluene, 0.6 mL of Hunig's base, and 20 mL of fresh GOPS, while keeping the flask under a slight positive pressure of argon by use of a septum. The flask is connected to a well-dried condenser that is already purged with argon. While the stirring bar and the slides move gently, the mixture is refluxed for 24 hrs under argon. After one day, the slides are removed from the flask (after the solution cools to room temperature). The slides are washed with methanol (50 mL×4), DCM (30 mL×3), and ether (30 mL×2). The slides are dried in a dessicator over $P_2O_5$.

Gradient GOPS:

Linear gradients are created from the reaction of hydroxylated ITO surfaces with GOPS in the following manner. A cylindrical flask with a marked scale of about 30 mL in volumetric size (larger size) with a small magnetic stirring bar, a cylindrical flask of smaller size with a small hole of a diameter of about 2 mm at the very bottom, and two ITO slides are dried in an oven for over a day at 120° C. The cylindrical flask of smaller size is placed inside of the larger cylindrical flask containing a magnetic stirrer. Two ITO slides are inserted into the inner flask with their faces (coated surface) out. As soon as all components are in the larger cylindrical flask (reactor), and while components are still hot, the system is closed with an appropriate size septum. Using a needle (20G1) through the septum, the reactor is flushed with argon for few minutes. A length of about 5 to 6 cm of this cylindrical flask is immersed into a silicon oil bath to heat the GOPS solution. Separately, a 50 mL round bottom flask with a magnetic stirring bar and a long needle of about 30 cm (diameter 20G, both ends open) are dried for over a day at 120° C. The round bottom flask is taken out of the oven, and while it is hot, the flask is flushed with argon for a few minutes. It is then filled with fresh GOPS (40 mL), and Hunig's base (1.2 mL), using oven dried syringes. While it is being kept under a positive pressure of argon, the solution is stirred for 5 minutes for mixing. The needle is taken out of the oven, and quickly one end of the dry needle is inserted into the round bottom flask through the septum. The other end of this needle is pushed into the reactor flask through the septum. The needle tip is pushed deep down to the bottom of the larger cylindrical flask through the outside space of the inner flask. Using a regular syringe needle (20G1) an argon outlet line is created and connected to a silicon bubbler.

The pressure of the whole system is monitored by observation of the bubbles, and is minimized after a few minutes of fast bubbling. The temperature of the oil bath on a hot plate is set up to 110° C. When the temperature of the oil bath is passing 105° C., the needle tip in the round bottom flask is dipped into the GOPS solution. The GOPS solution is smoothly transferred to the reactor by adjusting argon pressure in the GOPS-containing round bottom flask. It may be necessary to increase the pressure in the first few seconds to push the GOPS solution into the needle. A good addition speed is about 1.25 mL/min. Argon pressure is adjusted based on the speed of GOPS transfer. The total time is about 20 min for the 25 mL of GOPS solution to be transferred to the reactor and the slides are completely immersed into the solution.

As soon as the slides are covered with the solution transferred, the needle tip is removed from the remaining GOPS solution in the round bottom flask. After 10 min at 100 to 110° C., the argon outlet line of the reactor is switched with the argon inlet line of the round bottom flask. Now the argon inlet line is connected to the reactor and the outlet line to the round bottom flask. Again, by adjusting the argon pressure the GOPS solution is slowly removed from the reactor over 20 min at the same temperature. When the GOPS solution (about 25 mL) is completely transferred back to the round bottom flask, the oil bath is removed. The reactor is kept under a gentle argon flow for about 15 min to cool the assembly. The slides are washed with methanol, DCM, and ether as before, and dried in a dessicator over $P_2O_5$.

Target DNA is attached to the surface of ITO slides as a molecular probe. In a first example, the target DNA that is immobilized through a $-C_{12}-NH_2$ spacer unit is $dA_{20}$-$C_{12}-NH_2$, and $dT_{20}$-$C_{12}-NH_2$.

Hybridisation to ITO gradients with Immobilized $dT_{20}$

Immobilization of $dT_{20}$-$C_{12}-NH_2$

Complementary and non-complementary DNA is $dT_{20}$-$Cy_5$ and $dA_{20}$-$Cy_5$, respectively. Partially complementary DNA $dT_8A_3T_9$-$Cy_5$ has three mismatches in the centre when using the $dA_{20}$-$C_{12}-NH_2$ probe.

A gradient ITO slide containing GOPS is placed with its face up on a piece of wet Kimwipe™ paper in a petri dish filled with sterile water. Using a sterile sharp micro-scale plastic pipette tip, $dT_{20}$-linker ($-C_{12}-NH_2$)(55 nmol in 0.05 M-$H_2SO_4$) is spotted on the surface of the ITO in a row (drop size: 1–1.5 mm in diameter). In some cases, the probe to be immobilized is spread uniformly over the slide. To avoid being dried as soon as the spotting process is done, the slide is covered with the dish cover and wrapped tightly with aluminum foil. The slide is left in the dark overnight to maximize chemical immobilization. The slide is then washed gently with sterile water several times and dried in the air for 30 min. The slide is placed back into the petri dish.

Details of treatment of individual ITO slides as illustrated in FIGS. 3A–I are provided below.

Hybridisation of Complementary DNA

Figure 3E:
FIGS. 3A–I illustrate binding of target nucleic acid to gradient surfaces as described in Example 2.
Figure 3E:
Figure 3D:
Figure 3D:
Figure 3D:
Figure 3C:
Figure 3B:
Figure 3A:
Figure 3I:
Figure 3H:

Onto the spotted areas of $dT_{20}$-linker are placed drops of $dA_{20}$-$Cy_5$ (ca. 70 nmol in sterile water). In addition to covering the areas of $dT_{20}$-linker spots, another spot of $dA_{20}$-$Cy_5$ is placed on an edge area without $dT_{20}$-linker as a control. Again, the slide is left in the dark in the closed petri dish overnight to maximize hybridisation. In some cases, as described below, target nucleic acid is contacted with the slide over its entire surface. The slide is then washed gently with aqueous phosphate buffer solution (PBS) three times, and then dried for 30 min. The slide is scanned along with various control treatments with a microarray scanner (ChipReader™, Virtek Vision, Waterloo, ON, Canada) at the $Cy_5$ wavelength. FIGS. 3A–I show the results of scanning of the ITO slides for fluorescence. The darkest areas in FIGS. 3A–I, which were blue areas on the slides as originally visualized, represent no labelled DNA. Gray coloured areas in these figures (the darkerst of which were red on the slides as originally visualized) are due to fluorescent label and lighter to darker gray indicates increasing intensity of fluorescence. In FIGS. 3D, E and F target was spotted onto the slide.

Figure 3G:
Figure 3G:
Figure 3G:
Figure 3G:
Figure 3F:

In FIGS. 3GH and I target was uniformly contacted with the entire surface of the slide as described below.

ITO substrates illustrated in FIGS. 3A–I that contain probe density gradients are oriented in the figures such that the highest density is at the top of the substrate. Treatments illustrated in FIGS. 3A–I *include*:

(3A) Control treatment where a continuous gradient is formed by electrochemical hydroxylation, which is followed by GOPS treatment (reflux in toluene), after which the substrate is washed with methanol, DCM, and ether (no nucleic acid immobilized and no hybridisation) (No significant fluorescence is observed);

(3B) Control treatment with gradient preparation as in 3A with immobilization of $dT_{20}$-$C_{12}$—$NH_2$ (0.05M-$H_2SO_4$) followed by washing with sterile water (No significant fluorescence is observed);

(3C) Control treatment with continuous gradient formed by electrochemical hydroxylation, but no GOPS treatment, followed by immobilization of $dT_{20}$-$C_{12}$—$NH_2$ (0.05M-$H_2SO_4$) by spotting; treatment with $dA_{20}$-$Cy_5$, followed by washing with PBS (No significant fluorescence is observed);

(3D, three repetitions) Continuous gradient formed by electrochemical hydroxylation, followed by GOPS treatment (reflux in toluene), followed by immobilization of $dT_{20}$-$C_{12}$—$NH_2$ (0.05M-$H_2SO_4$) by spotting, followed by treatment with $dA_{20}$-$Cy_5$, and washing with PBS; Fluorescence is detected within spots on each ITO substrate shown with intensity of fluorescence, indicative of increased amounts of hybridized target and increased probe density; increasing from bottom to top in spots along the substrates;

(3E, two repetitions) Continuous gradient formed by GOPS treatment (neat with Hunig's base, 110° C., 60 min) after hydroxylation by plasma cleaning (15 min, followed by immobilization of $dT_{20}$-$C_{12}$—$NH_2$ (0.05M-$H_2SO_4$) by spotting; treatment with $dA_{20}$-$Cy_5$, followed by washing with PBS; Fluorescence is detected within spots on each ITO substrate shown with intensity of fluorescence increasing from bottom to top of the substrates (3F) No gradient control; Homogeneous hydroxylation by electrochemical method followed by treatment as for experiment (3D) to provide a uniform density immobilization layer; Fluorescence is detected within spots on the ITO substrate shown with uniform intensity of fluorescence increasing along the length (top to bottom) of the ITO slide;

(3G, four repetitions) Continuous gradient formed by electrochemical hydroxylation, followed with GOPS treatment (reflux in toluene), immobilizing $dT_{20}$-$C_{12}$—$NH_2$ (0.05M-$H_2SO_4$), followed by treatment with $dA_{20}$-$Cy_5$, and washing with PBS; DNA to be immobilized was not spotted, but spread along the slide, and the entire slide surface was thereafter treated with $dA_{20}$-$Cy_5$, followed by washing with PBS; A gradient of increasing probe density as indicated by increasing fluorescence intensity is observed from bottom to top of the ITO slides shown;

(3H) Control treatment; ITO slide prepared as for (3G), but only the upper half of the slide is electrochemically homogeneously hydroxylated before GOPS treatment, $dT_{20}$-$C_{12}$—$NH_2$ (0.05M-$H_2SO_4$) immobilized by spreading over entire surface; ),followed by treatment of the entire slide with $dA_{20}$-$Cy_5$, and washing with PBS; Uniform fluorescence is observed in the upper portion of the ITO slide; and (3I) Illustrative results for hybridisation of a partially complementary DNA $dT_8A_3T_9$-$Cy_5$, to a gradient formed as in 3H carrying immobilized $dT_{20}$; Fluorescence intensity is localized to a band (10) within the density gradient.

Those of ordinary skill in the art will appreciate that methods, procedures, devices, instrumentation, materials, and reagents other than those specifically described herein can readily be employed in the practice of this invention as broadly described herein without undue experimentation. All methods, procedures, devices, instrumentation, materials, and reagents that can be readily adapted to the practice of this invention or that are recognized in the art to be functional equivalents of the specific methods, procedures, devices, instrumentation, materials, and reagents disclosed herein are intended to be encompassed by this invention. All references cited herein are incorporated by reference herein to the extent that they are not inconsistent with the description herein.

The invention claimed is:

1. A hybridization platform comprising:
   a planar support; and
   an immobilized layer of single stranded nucleic acids or nucleic acid analogs formed on the surface of the planar support;
   wherein the immobilized layer is formed as either a) a continuous layer on the surface or b) as discrete regions on the surface;
   the nucleic acids or nucleic acid analogs being arranged as the continuous layer, or as each region, such that the one or more parameters selected from the density, sequence, orientation or structure of the nucleic acid or nucleic acid analogs are spatially varied as a continuum in the continuous layer or in each region in one or both of a first and second dimension across the surface of the planar support so as to form at least one gradient of the one or more parameters within the continuous layer or each region; and
   the one or more selected parameters includes the density of the nucleic acid or nucleic acid analogs.

2. The hybridization platform of claim 1 which comprises a first gradient and a second gradient, wherein the first gradient is formed by spatially varying the density of the nucleic acids or nucleic acid analogs.

3. The hybridization platform of claim 2 wherein the immobilized layer further comprises polyelectrolyte immobilized to the surface of the planar support such that a further gradient is formed by spatially varying the concentration of polyelectrolyte.

4. The hybridization platform of claim 2, wherein the at least on gradient spans an average nearest neighbour separation of from about 2 mm to over 40 nm.

5. The hybridization platform of claim 2 wherein the planar support is fused silica, quartz, silicon, glass, a plastic, a metal, a transparent electrode, a ceramic, a semiconductor, a conductive form of carbon, paper, a conductive polymer, or a waveguide operating in either the evanescent mode or direct mode of excitation.

6. The hybridization platform of claim 5 wherein the at least one gradient is formed by dip-casting, through gradients of light activation, by spraying, rolling, capping, sequence annealing, sequence degradation, sequence extension or combinations thereof.

7. The hybridization platform of claim 6 wherein the nucleic acids or nucleic acid analogs are immobilized to the surface by adsorption, absorption, ionic bonding, covalent bonding, avidin-biotin, or thiol-gold interactions.

8. The hybridization platform of claim 7 wherein the nucleic acids or nucleic acid analogs are immobilized to the surface by covalent bonding.

9. The hybridization platform of claim 5 wherein the planar support is a waveguide, operating in either the evanescent mode or direct mode of excitation.

10. The hybridization platform of claim 2 wherein the first and second gradients are formed in orthogonal dimensions of the surface.

11. The hybridization platform of claim 2 wherein the second gradient is formed by varying the sequence of the nucleic acids or nucleic acid analogs.

12. The hybridization platform of claim 2 wherein the immobilized layer further comprises detectable labels that indicate binding of target molecules to the nucleic acids or nucleic acid analogs.

13. The hybridization platform of claim 2 further comprising detectable labels bound to the nucleic acids or nucleic acid analogs.

14. The hybridization platform of claim 13 wherein the detectable labels are fluorescent labels tethered to the nucleic acid or nucleic acid analogs.

15. The hybridization platform of claim 2 further comprising fluorescent labels immobilized to the surface.

16. The hybridization platform of claim 2 further comprising a further gradient formed by varying the density of detectable labels tethered to the nucleic acids or nucleic acid analogs.

17. The hybridization platform of claim 16 wherein the detectable labels are fluorescent molecules.

18. The hybridization platform of claim 2 further comprising a reference region in the at least one gradient.

19. The hybridization platform of claim 2 wherein the second gradient is formed by varying the length of the nucleic acids or nucleic acid analogs in the immobilized layer.

20. The hybridization platform of claim 19 wherein the second gradient is formed by varying the length of the nucleic acids or nucleic acid analogs in single base increments.

21. The hybridization platform of claim 20 wherein the second gradient spans 1,000 or more bases.

22. The hybridization platform of claim 20 wherein the second gradient spans 100 or more bases.

23. The hybridization platform of claim 20 wherein the second gradient spans 10 to about 50 bases.

24. The hybridization platform of claim 1 wherein the immobilized layer is formed as a continuous layer on the surface.

25. The hybridization platform of claim 1 wherein the immobilized layer is formed as discrete regions on the surface.

26. A biosensor for detection of one or more target molecules comprising:
 a planar support; and
 an immobilized layer of single stranded nucleic acids or nucleic acid analogs formed on the surface of the planar support and capable of hybridizing to the one or more target molecules;
 wherein the immobilized layer is formed as either a) a continuous layer on the surface or b) as discrete regions on the surface;
 the nucleic acids or nucleic acid analogs being arranged as the continuous layer, or as each region, such that the one or more parameters selected from the density, sequence, orientation or structure of the nucleic acid or nucleic acid analogs are spatially varied as a continuum in the continuous layer or in each region in one or both of a first and second dimension across the surface of the planar support so as to form at least one gradient of the one or more parameters within the continuous layer or each region; and
 the one or more selected parameters includes the density of the nucleic acid or nucleic acid analogs.

27. The biosensor of claim 26 further comprising detectable labels for indicating binding of the one or more target molecules to the nucleic acids or nucleic acid analogs.

28. A kit for conducting an assay for detecting and quantifying one or more target molecules in a sample which comprises:
 a planar support; and
 an immobilized layer of single stranded nucleic acids or nucleic acid analogs formed on the surface of the planar support and capable of hybridizing to the one or more target molecules;
 wherein the immobilized layer is formed as either a) a continuous layer on the surface or b) as discrete regions on the surface;
 the nucleic acids or nucleic acid analogs being arranged as the continuous layer, or as each region, such that the one or more parameters selected from the density, sequence, orientation or structure of the nucleic acid or nucleic acid analogs are spatially varied as a continuum in the continuous layer or in each region in one or both of a first and second dimension across the surface of the planar support so as to form at least one gradient of the one or more parameters within the continuous layer or each region; and
 the one or more selected parameters includes the density of the nucleic acid or nucleic acid analogs.

29. The kit of claim 28 further comprising one or more reagents to detect and quantify the one or more target molecules hybridized to the nucleic acids or nucleic acid analogs.

30. A method of forming a hybridization platform comprising:
 providing a planar support, and
 forming on the surface of the planar support an immobilized layer of single stranded nucleic acids or nucleic acid analogs, the immobilized layer being formed either as a) a continuous layer on the surface or b) as discrete regions on the surface, the continuous layer or each region being arranged such that one or more parameters selected from the density, sequence, orientation or structure of the nucleic acid or nucleic acid analogs are spatially varied as a continuum in the continuous layer or in each region in one or both of a first and second dimension across the surface of the planar support so as to form at least one gradient of the one or more parameters within the continuous layer or each region, wherein the one or more selected parameters includes the density of the nucleic acids or nucleic acid analogs.

* * * * *